United States Patent
Hino et al.

(10) Patent No.: US 8,419,452 B2
(45) Date of Patent: Apr. 16, 2013

(54) ELECTRIC CONNECTOR AND ENDOSCOPE

(75) Inventors: Kazuhiko Hino, Hachioji (JP); Takashi Sawai, Fuchu (JP); Akihiro Shimazu, Hachioji (JP); Tsuyoshi Mandai, Kawasaki (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/400,798

(22) Filed: Feb. 21, 2012

(65) Prior Publication Data

US 2012/0208403 A1   Aug. 16, 2012

Related U.S. Application Data

(63) Continuation of application No. PCT/JP2010/060378, filed on Jun. 18, 2010.

(30) Foreign Application Priority Data

Sep. 1, 2009   (JP) .................................. 2009-201922

(51) Int. Cl.
*H01R 13/44* (2006.01)

(52) U.S. Cl.
USPC ........................................................ 439/141

(58) Field of Classification Search .................. 439/140, 439/141
See application file for complete search history.

(56) References Cited

U.S. PATENT DOCUMENTS

| | | | | |
|---|---|---|---|---|
| 2,892,990 A * | 6/1959 | Werndl | ......................... | 439/265 |
| 3,497,866 A * | 2/1970 | Patton, Jr. | ..................... | 439/680 |
| 3,754,205 A * | 8/1973 | Lenkey | ......................... | 439/141 |
| 3,831,133 A * | 8/1974 | Grundfest | ..................... | 439/680 |
| 5,140,659 A * | 8/1992 | Minds et al. | .................... | 385/66 |
| 5,423,689 A * | 6/1995 | Valentino | ...................... | 439/141 |
| 5,871,371 A * | 2/1999 | Rothenberger et al. | ....... | 439/579 |
| 6,420,888 B1 * | 7/2002 | Griffin et al. | ............. | 324/754.11 |
| 6,767,227 B2 * | 7/2004 | Yamaguchi et al. | .......... | 439/137 |
| 7,300,292 B2 * | 11/2007 | Nagata | ......................... | 439/141 |
| 8,079,855 B2 * | 12/2011 | Pfeiffer | ......................... | 439/140 |

FOREIGN PATENT DOCUMENTS

JP   3-62451   7/1991
(Continued)

OTHER PUBLICATIONS

Japanese Office Action dated May 22, 2012 from corresponding Japanese Patent Application No. 2011-529843.

(Continued)

*Primary Examiner* — Phuong Dinh
(74) *Attorney, Agent, or Firm* — Scully, Scott, Murphy & Presser, P.C.

(57) ABSTRACT

An electric connector portion includes first and second electric contact portions which are connectable to first and second target electric contact portions, respectively, and a protective member which is movable from a protecting position where the first and second electric contact portions are protected to an opening position where the first and second electric contact portions are opened in a moving direction extending from the first electric contact portion side to the second electric contact portion side, wherein the protective member includes an opening portion which is configured to open the second electric contact portion when the protective member is arranged at the opening position.

6 Claims, 11 Drawing Sheets

FOREIGN PATENT DOCUMENTS

| | | |
|---|---|---|
| JP | 6-5328 | 1/1994 |
| JP | 9-326279 | 12/1997 |
| JP | 2000-171724 | 6/2000 |
| JP | 2008-278971 | 11/2008 |
| JP | 2010-86856 A | 4/2012 |

OTHER PUBLICATIONS

International Search Report dated Aug. 10, 2010 filed in PCT/JP2010/060378.

\* cited by examiner

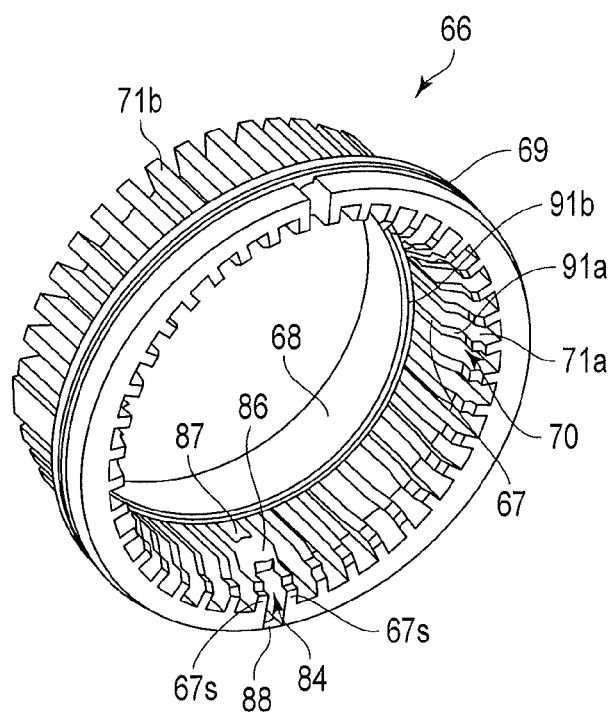
F I G. 4
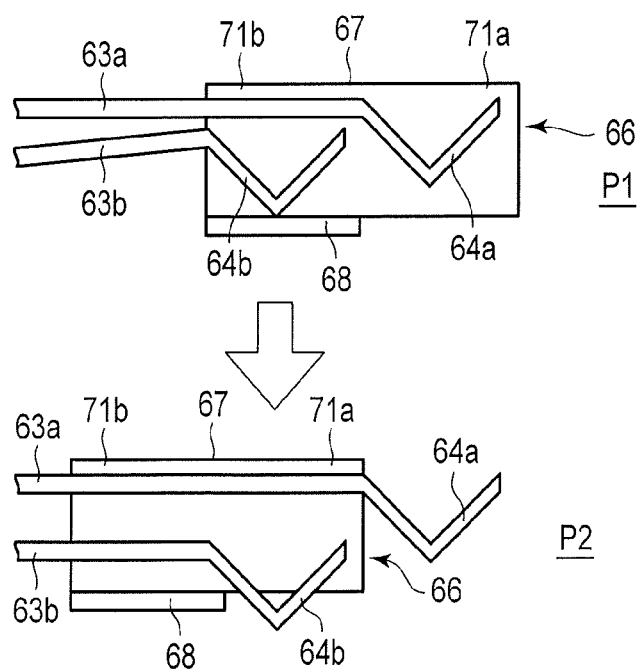
F I G. 5

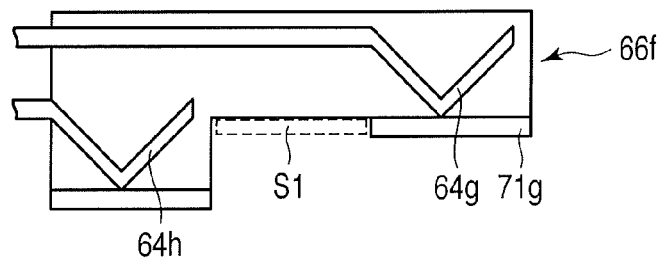
F I G. 10
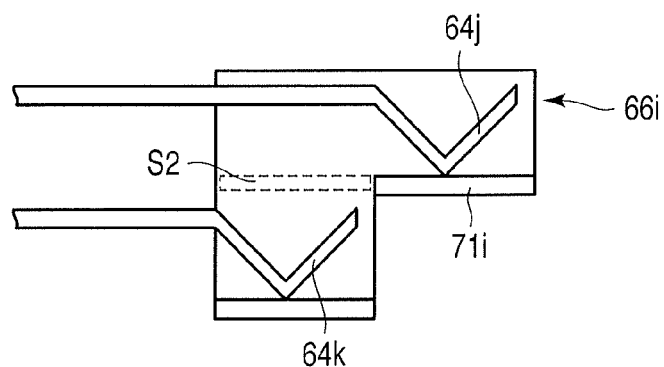
F I G. 11
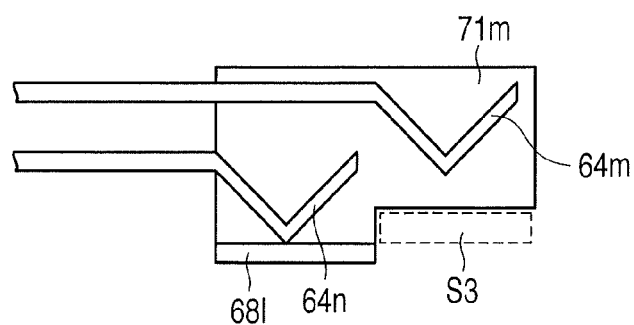
F I G. 12

US 8,419,452 B2

ELECTRIC CONNECTOR AND ENDOSCOPE

CROSS-REFERENCE TO RELATED APPLICATIONS

This is a Continuation Application of PCT Application No. PCT/JP2010/60378, filed Jun. 18, 2010, which was published under PCT Article 21(2) in Japanese.

This application is based upon and claims the benefit of priority from the prior Japanese Patent Application No. 2009-201922, filed Sep. 1, 2009, the entire contents of which are incorporated herein by reference.

BACKGROUND OF THE INVENTION

1. Field of the Invention

The present invention relates to an electric connector including a protective member which protects an electric contact portion and which moves to the electric connector and opens the electric contact portion when the electric connector is connected to a target connector portion.

2. Description of the Related Art

Jpn. Pat. Appln. KOKAI Publication No. hei 6-5328 discloses an electric connector for use in an automobile and others. In the electric connector, a window from which a terminal is exposed is formed in a male type connector housing and the window is opened/closed by a protective cover in a male type connector. In the male type connector, the window is closed by the protective cover to protect the terminal when separated from a female type connector, and the protective cover is pushed up by a female type connector housing to open the window and the terminal is exposed when connected to the female type connector.

Jpn. Pat. Appln. KOKAI Publication No. 2000-171724 discloses an electric connector which has the same configuration as that of the electric connector according to Patent Literature 1 (Jpn. Pat. Appln. KOKAI Publication No. hei 6-5328) and is used in an endoscope and the like. In this electric connector, a circuit board including a contact electrode is arranged in a connector main body, and the circuit board is covered or exposed by advancing and retreating a protective cover. In the connector main body, the protective cover is advanced to cover the circuit board and the contact electric is protected when separated from a target connector, and the protective cover is retreated by the target connector to expose the circuit board and the contact electrode is exposed when connected to the target connector.

BRIEF SUMMARY OF THE INVENTION

In one embodiment of the present invention, an electric connector portion includes first and second electric contact portions which are connectable to first and second target electric contact portions, respectively; and a protective member which is movable from a protecting position where the first and second electric contact portions are protected to an opening position where the first and second electric contact portions are opened in a moving direction extending from the first electric contact portion side to the second electric contact portion side, wherein the protective member includes an opening portion which is configured to open the second electric contact portion when the protective member is arranged at the opening position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view showing a shutter according to the embodiment of the present invention;

FIG. 5 is a schematic view showing a receptacle contact and the shutter according to the embodiment of the present invention;

FIG. 10 is a schematic view showing a receptacle contact and a shutter according to a first modification of the present invention;

FIG. 11 is a schematic view showing a receptacle contact and a shutter according to a second modification of the present invention;

FIG. 12 is a schematic view showing a receptacle contact and a shutter according to a third modification of the present invention;

DETAILED DESCRIPTION OF THE INVENTION

[One Embodiment of Present Invention]

An embodiment according to the present invention will now be described with reference to the drawings.

The embodiment according to the present invention will be explained with reference to FIG. 1 to FIG. 12.

Figure 1:
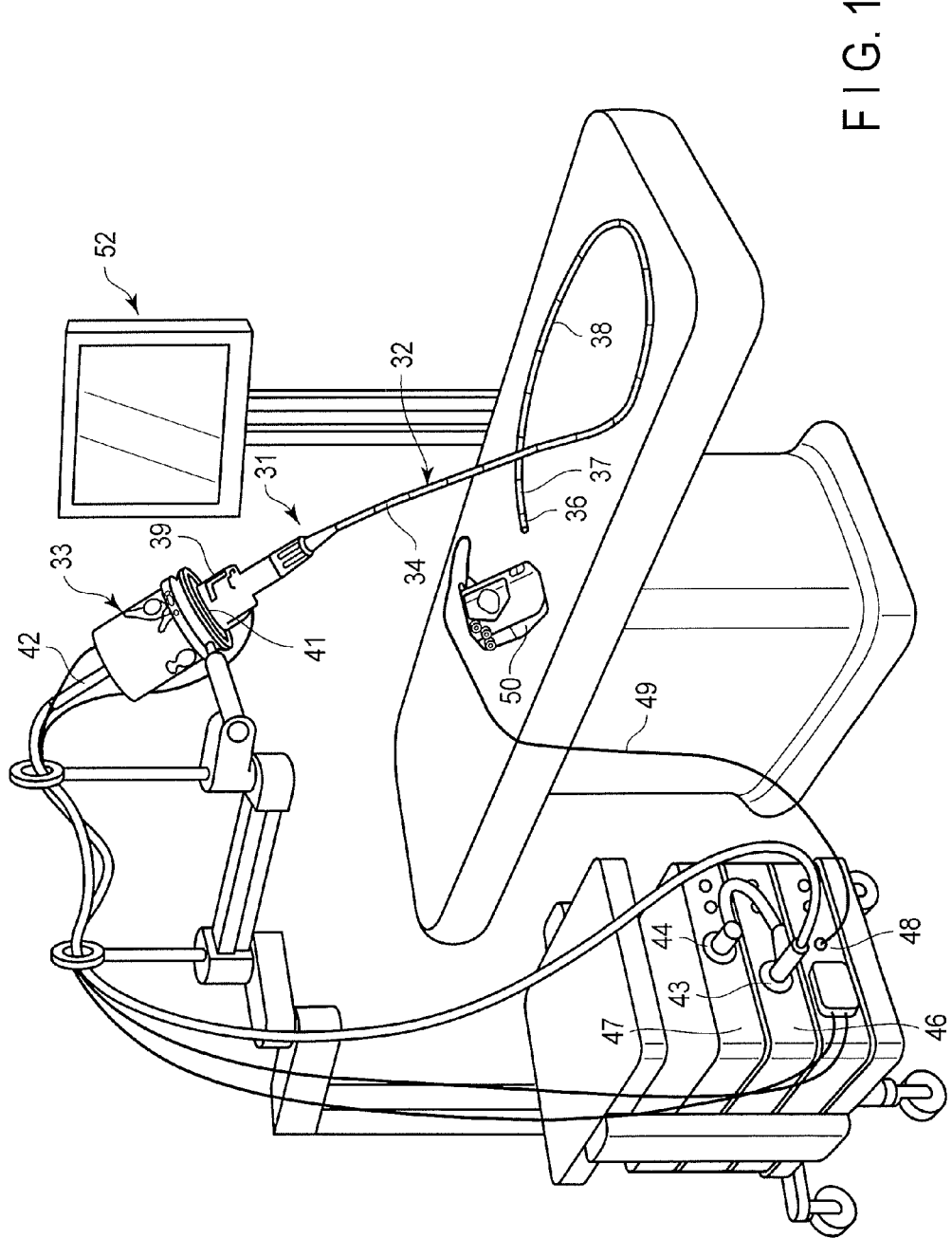
FIG. 1 is a perspective view showing an endoscopic system according to an embodiment of the present invention.

Referring to FIG. 1, an endoscopic system includes an assembly type endoscope 31. The assembly type endoscope 31 includes an insertion unit 32 and a drive unit 33. The insertion unit 32 includes an elongated insertion portion 34 which is inserted into a body cavity. In the insertion portion 34, a distal end hard portion 36 having hardness, a bending portion 37 which is operated to bend, and a flexible tube portion 38 which is long and flexible are continuously provided from a distal end side toward a proximal end side. An inserting/removing portion 39 is coupled with a proximal end portion of the insertion portion 34. The insertion unit 32 is attachable to/detachable from the drive unit 33, and the convex inserting/removing portion 39 of the insertion unit 32 can be inserted into/removed from a concave insertion/removal receiving portion 41 in the drive unit 33. A universal cable 42 is extended from the drive unit 33, and a light source connector 43 and a video connector 44 are arranged at an extended end portion of the universal cable 42. The light source connector 43 is connected to a light source device 46, and the video connector 44 is connected to a video processor 47. It is to be noted that the light source device 46 and the video processor 47 are connected to a system controller 48 and an operating section 50 configured to operate the endoscopic system is connected to the system controller 48 through an operation cable 49.

Illumination light generated by the light source device 46 is supplied to an illumination optical system in the distal end hard portion 36 to be applied to an observation target. Further, a drive signal generated by the video processor 47 is output to an imaging unit in the distal end hard portion 36. The imaging unit which has received the drive signal acquires an observation image to generate an image signal, the generated image signal is output to the video processor 47, and the video processor 47 displays an observation image on a monitor 52.

In the drive unit 33 and the insertion unit 32, a light guide which guides illumination light and an electric cable which transmits various kinds of signals are extended. Furthermore, a light connector and an electric connector are formed to the insertion/removal receiving portion 41 of the drive unit 33 and the inserting/removing portion 39 of the insertion unit 32, and the light connector connects and separates the light guide of the drive unit 33 with respect to the light guide of the insertion unit 32, and the electric connector connects and separates the electric cable of the drive unit 33 with respect to the electric cable of the insertion unit 32 in accordance with insertion/removal of the inserting/removing portion 39 with respect to the insertion/removal receiving portion 41.

The electric connector will now be described in detail with reference to FIG. 2 to FIG. 5.

A plug 53 as a target electrical connector portion is formed in the inserting/removing portion 39 of the insertion unit 32, and a receptacle 54 as an electrical connector portion is formed in the insertion/removal receiving portion 41 of the drive unit 33.

Figure 2:
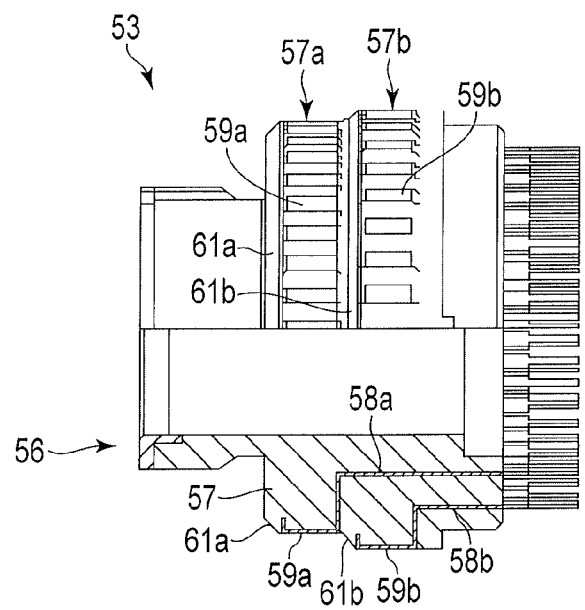
FIG. 2 is a longitudinal cross-sectional and side elevational view showing a plug according the embodiment of the present invention.

The plug 53 will now be described in detail with reference to FIG. 2.

A plug-side electric connecting portion is formed in the plug 53. That is, the plug 53 includes a cylindrical plug housing 56, and a contact arranging portion 57 having a large diameter is formed in an axially inner portion in the plug housing 56. First and second contact regions 57a and 57b are formed on an outer peripheral portion of the contact arranging portion 57. Both the contact regions 57a and 57b extend on the entire circumference of the contact arranging portion 57, the first contact region 57a is arranged on the axially outer side, the second contact region 57b is arranged on the axially inner side, and an outside diameter of the second contact region 57b is larger than an outside diameter of the first contact region 57a. Further, many first and second plug contacts 58a and 58b are buried in the contact arranging portion 57. Each of the contact plugs 58a and 58b has a rectangular column shape and is extended in the axial direction, and many first plug contacts 58a and many second contact plugs 58b are provided in parallel with the axial direction, respectively. A corresponding second plug contact 58b is arranged on the axially inner side and the radially outer side with respect to a predetermined first plug contact 58a in parallel with the axial direction. One surface portion of the axially outer end part of each of the first and second plug contacts 58a and 58b is exposed in each of the first and second contact regions 57a and 57b to form each of first and second plug contacts 59a and 59b as electric contact portions which extend in the axial direction and are substantially orthogonal to the radial direction. A corresponding second plug contact 59b is arranged on the axially inner side and the radially outer side with respect to a predetermined first plug contact 59a in parallel with the axial direction.

Further, a drive portion is formed in the plug 53. That is, a first drive surface 61a inclined toward the radially outer side as seen in axially inwards is formed on the outer peripheral portion of the contact arranging portion 57 at the axially outer end part. Furthermore, a second drive surface 61b inclined toward the radially outer side as seen in axially inwards is formed between the first contact region 57a and the second contact region 57b on the outer peripheral portion of the contact arranging portion 57.

The receptacle 54 will now be described in detail with reference to FIG. 3 to FIG. 5.

Figure 3:
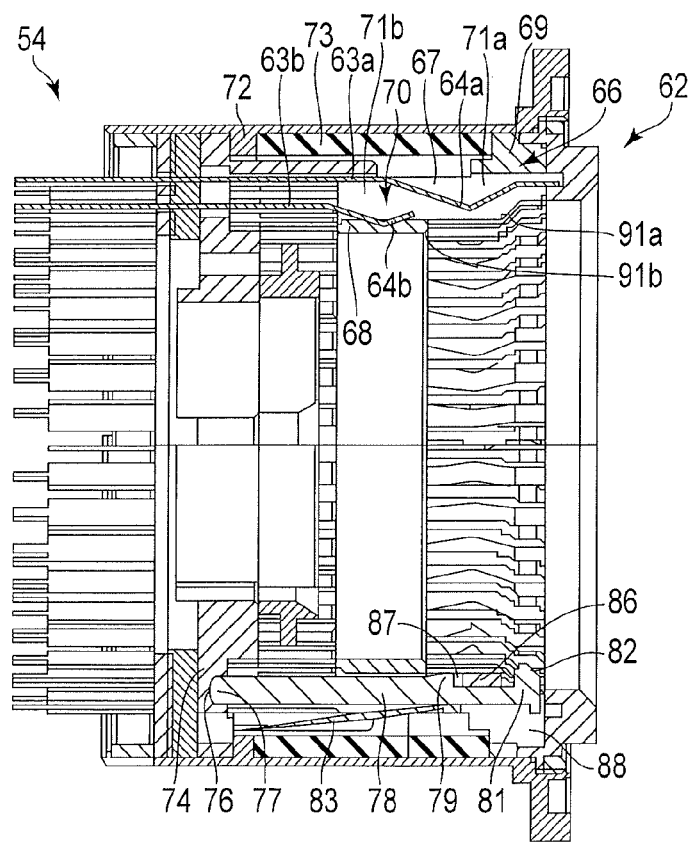
FIG. 3 is a longitudinal cross-sectional view showing a receptacle according to the embodiment of the present invention.

Referring to FIG. 3, a receptacle-side electric connecting portion electrically connected to a plug-side electric connecting portion is formed in the receptacle 54. That is, the receptacle 54 includes a cylindrical receptacle housing 62, and many first and second receptacle contacts 63a and 63b are arranged on the inner peripheral portion of the receptacle housing 62. Each of the receptacle contacts 63a and 63b has a long tabular shape orthogonal to the radial direction and is extended in the axial direction, and many first receptacle contacts 63a and many second receptacle contacts 63b are provided in parallel with the circumferential direction, respectively. A corresponding second receptacle contact 63b is arranged on the axially inner side and the radially inner side with respect to a predetermined first receptacle contact 63a in parallel with the axial direction. An axially outer end portion of each of the first and second receptacle contacts 63a and 63b has a radially and inwardly protruding V-like shape and forms each of the first and second receptacle contacts 64a and 64b as an electrical contact. The receptacle contacts 64a and 64b are radially and inwardly opened and can come into contact with the target plug contacts 58a and 58b, and the radial inward direction is an opening direction. A corresponding second receptacle contact 64b is arranged on the axially inner side and the radially inner side with respect to a predetermined first receptacle contact 64a in parallel with the axial direction.

Referring to FIG. 3 to FIG. 5, a shutter mechanism which protects and opens the receptacle contacts 64a and 64b is formed in the receptacle 54.

Referring to FIG. 3 and FIG. 4, a shutter 66 as a protective member is arranged on the inner peripheral portion of the receptacle housing 62. The shutter 66 can slide in the axial direction with respect to the receptacle housing 62, and it can be arranged at a protecting position on the axially outer side and an opening position on the axially inner side.

The shutter 66 includes many sidewalls 67, an inner peripheral wall 68, and an outer peripheral wall 69. The sidewalls 67 are substantially orthogonal to the circumferential direction and extended in the axial direction, and many sidewalls 67 are provided in parallel with the circumferential direction. Each receptacle contact accommodation space 70 which accommodates the receptacle contact 63a or 63b is formed between the two sidewalls 67 adjacent to each other. An axially outer side portion of each sidewall 67 will be referred to as a first sidewall portion 71a and an axially inner side portion of the same will be referred to as a second sidewall portion 71b hereinafter. The inner peripheral wall 68 is coupled with a radially inner side surface of each second sidewall portion 71b, has an axial width substantially equal to an axial length of each second sidewall portion 71b, and extends over the entire circumference. The outer peripheral wall 69 is coupled with a radially outer side surface of an axially outer side part of each first sidewall portion 71a, has an axial width sufficiently shorter than an axial length of each first sidewall portion 71a, and extends over the entire circumference.

Referring to FIG. 5, when the shutter 66 is arranged at the protecting position P1 on the axially outer side, the first receptacle contact 64a is arranged between the two first sidewall portions 71a adjacent to each other, and the second receptacle contact 64b is arranged between the two second sidewall portions 71b adjacent to each other. The radially inner side surface of the first sidewall portion 71a is arranged on the radially inner side as compared with the V-shaped radially inner end portion of the first receptacle contact 64a. In this manner, the first sidewall portion 71a functions as a first protecting portion which protects the first receptacle contact 64a. Furthermore, the inner peripheral wall 68 is arranged on the radially inner side of the second receptacle contact 64b. It is to be noted that the second receptacle contact 64b is pressed radially outwards by the inner peripheral wall 68 and displaced and arranged radially outwards by elastic deformation of the second receptacle contact 63b. In this manner, the inner peripheral wall 68 functions as a second protecting portion which protects the second receptacle contact 64b.

When the shutter 66 is arranged at the opening position P2 on the axially inner side, the first and second receptacle contacts 64a and 64b are opened in the radially inward direction forming the opening direction. That is, the first sidewall portion 71a forming the first protecting portion is arranged on the axially inner side as compared with the first receptacle contact 64a, and the entire first receptacle contact 64a is arranged to protrude axially outwards from an axially outer end opening between the two first sidewall portions 71a adjacent to each other. The inner peripheral wall 68 forming the second protecting portion is arranged on the axially inner side as compared with each second receptacle contact 64b, each first sidewall portion 71a forming the first protecting portion is arranged to overlap the second receptacle contact 64b in the axial direction, and the second receptacle contact 64b is arranged between the two first sidewall portions 71a adjacent to each other. The radially inward pressing force applied by the inner peripheral wall 68 is released, and each receptacle contact 64b is restored to and arranged at a natural position on the radially outer side by restoration deformation of the second receptacle contact 63b. Moreover, the V-shaped radially inner end portion of the second receptacle contact 64b is arranged on the radially inner side as compared with the radially inner side surface of each first sidewall portion 71a, and it is arranged to protrude radially inwards from a radially inner opening between the two first sidewall portions 71a adjacent to each other. In this manner, each first sidewall portion 71a forming the first protecting portion also functions as an opening portion which opens the second receptacle contact 64b in the radially inward direction forming the opening direction when the shutter 66 is arranged at the opening position.

Again referring to FIG. 3 and FIG. 4, a regulation mechanism which regulates movement of the shutter 66 to hold the shutter 66 at the protecting position when separated from the plug 53 and releases the regulation of movement of the shutter 66 when connected to the plug 53 is formed in the receptacle 54.

An elastic load support portion 72 is formed on an inner peripheral surface of the outer wall portion of the receptacle housing 62. The elastic load support portion 72 protrudes radially inwards and is extended over the entire circumference. The elastic load support portion 72 is arranged on the axially inner side of the axially inner end annular surface of the outer peripheral wall 69 of the shutter 66. A cylindrical shutter sustention member 73 constituted of an elastic member is compressed and arranged between the elastic load support portion 72 and the outer peripheral wall 69. The shutter 66 is constantly compressed to the protecting position on the axially outer side by the shutter sustention member 73.

An annular disk-like partition wall portion 74 which is substantially orthogonal to the axial direction is formed on an axially inner end portion of the receptacle housing 62. A circumferential concave surface 76 as a sliding concave portion is formed on the axially outer end surface portion of the partition wall portion 74. The circumferential concave surface 76 has a circumferential planar shape having a central axis substantially orthogonal to the axial direction and the radial direction. On the other hand, a circumferential convex surface 77 as a sliding convex portion is formed on one end portion of a rod-like stopper 78 as a regulation member. The circumferential convex surface 77 has a circumferential planar shape having a central axis substantially orthogonal to the axial direction of the stopper 78. The circumferential convex surface 77 is inserted into the circumferential concave surface 76 to be slidably supported. The stopper 78 can revolve about the axially inner end portion by sliding of the circumferential convex surface 77 on the circumferential convex surface 76, and it can be arranged at a regulating position substantially parallel to the axial direction and a releasing position where the axially outer end portion is displaced from the regulating position to the radially outer side. A regulation convex portion 79 protruding radially inward is formed on the axially intermediate portion of the stopper 78. Additionally, in the stopper 78, a release receiving portion 81 protruding radially inwards is formed on the axially outer end portion. A release receiving surface 82 which is inclined toward the radially inner side as seen in axially inwards is formed on a portion of the axially outer side and the radially inner side of the release receiving portion 81. Further, a stopper sustention member 83 constituted of an elastic member is provided on the axially outer end surface portion of the partition wall portion 74 of the receptacle housing 62 to protrude toward the axially outer side. The stopper 78 is constantly compressed to the regulating position by the stopper sustention member 83.

In regard to the shutter 66, the stopper 78 is accommodated in place of the first and second receptacle contacts 64a and 64b between a predetermined set of sidewalls 67s. A regulation receiving wall 86 is formed between the set of sidewalls 67s. The regulation receiving wall 86 is arranged on the radially inner side end portion of the stopper accommodation space 84, and it is arranged between the inner peripheral wall 68 and the outer peripheral wall 69 to be apart from the inner peripheral wall 68 by a predetermined distance in the axial direction. A regulation convex portion accommodation space 87 is formed between the regulation receiving wall 86 and the inner peripheral wall 68. Furthermore, a notch portion 88 having a through groove shape is formed in the outer peripheral wall 69 to overlap the stopper accommodation space 84 as seen in the radial direction.

The regulation convex portion 79 is inserted into the regulation convex portion accommodation space 87 when the stopper 78 is arranged at the regulating position. The regulation convex portion 79 is arranged on the axially inner side of the regulation receiving wall 86, and axial movement of the shutter 66 is restricted when the regulation receiving wall 86 abuts on the regulation convex portion 79. Furthermore, the release receiving portion 81 is protruded radially inwards from the space between the sidewalls 67s to get across the regulation receiving wall 86. When the stopper 78 is arranged at the releasing position, the regulation convex portion 79 is removed from the regulation convex portion accommodation space 87, thereby releasing the restriction of the axial movement of the shutter 66. Moreover, the release receiving portion 81 is removed radially outwards from the space between the sidewalls 67 and arranged in the notch portion 88 of the outer peripheral wall 69.

Referring to FIG. 3 and FIG. 4, an opening receiving portion as a driven receiving portion is driven by the drive portion of the plug 53 to move the shutter 66 to the opening position. That is, first opening receiving surfaces 91a are formed on the axially outer end portions of all the sidewalls 67 and 67s of the shutter 66, and a second opening receiving surface 91b is formed on the axially outer end portion of the inner peripheral wall 68 of the shutter 66. The first and second opening receiving surfaces 91a and 91b are inclined radially inwards forming the opening direction of the receptacle contacts 64a and 64b as seen in axially inwards serving as the connecting direction of the plug 53.

Figure 6:
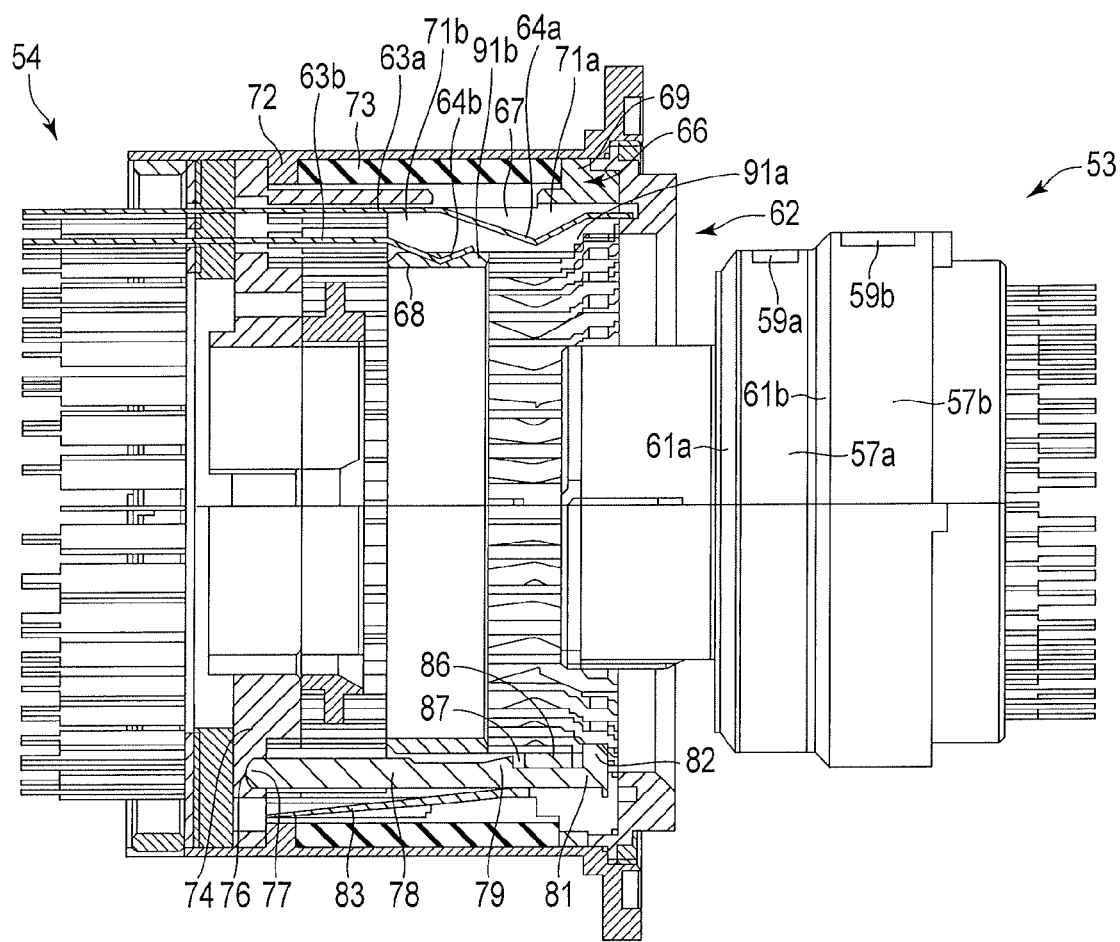
FIG. 6 is a side elevational and longitudinal cross-sectional view showing an electrical connector in a separated state according to the embodiment of the present invention.
Figure 7:
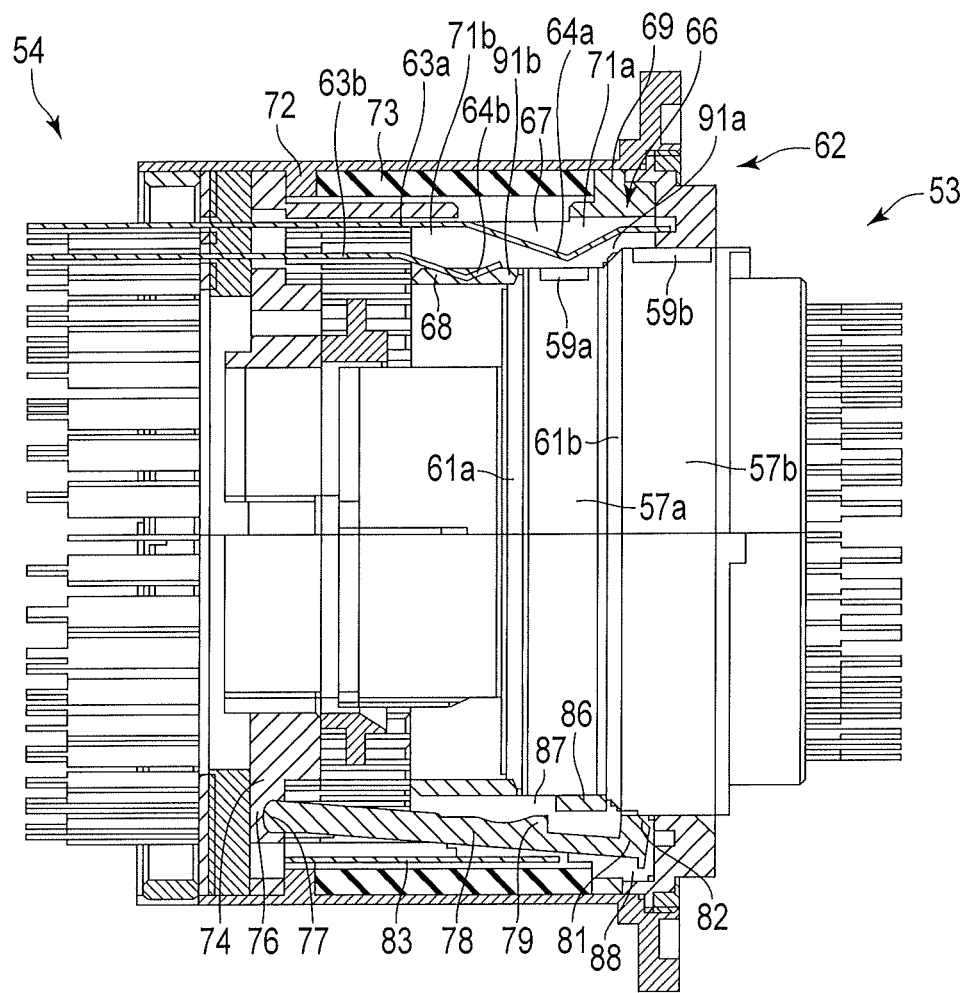
FIG. 7 is a side elevational and longitudinal cross-sectional view showing the electrical connector in a contact state according to the embodiment of the present invention.
Figure 8:
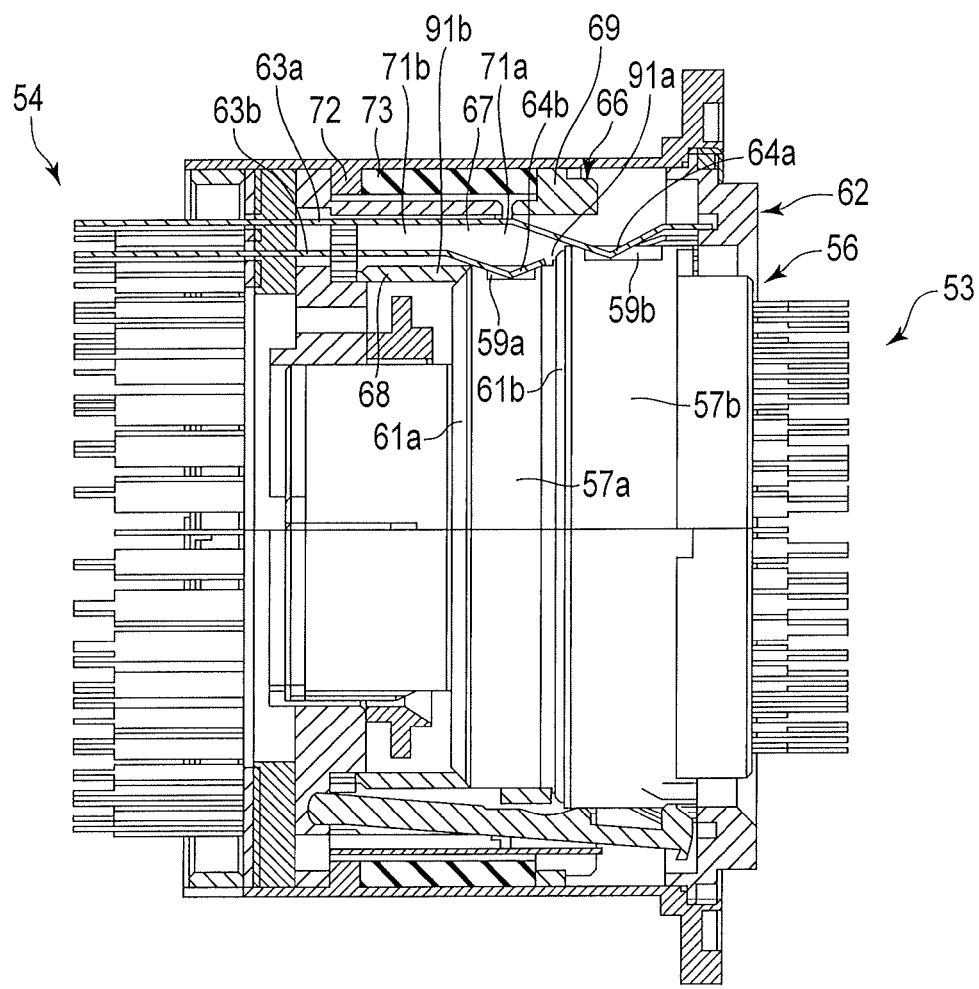
FIG. 8 is a side elevational and longitudinal cross-sectional view showing the electrical connector in a connected state according to the embodiment of the present invention.

Referring to FIG. 6 to FIG. 8, a connecting operation of the electric connector will now be described.

As shown in FIG. 6, when the plug 53 is separated from the receptacle 54, the shutter 66 is held at the holding position and the first and second receptacle contacts 64a and 64b are protected by the shutter 66 in the receptacle 54. That is, the shutter 66 is arranged at the protecting position on the axially outer side by the shutter sustention member 73. Further, the stopper 78 is arranged at the regulating position by the stopper sustention member 83, and the regulation convex portion 79 of the stopper 78 is inserted into the regulation convex portion accommodation space 87 of the shutter 66 and arranged on the axially inner side of the regulation receiving wall 86 of the shutter 66. When the regulation receiving wall 86 abuts on the regulation convex portion 79, movement of the shutter 66 in the axially inward direction is regulated. The first receptacle contact 64a is arranged between the adjacent first sidewall portions 71a of the shutter 66, and the radially inner side surface of each first sidewall portion 71a is arranged on the radially inner side as compared with the radially inner end portion of the first receptacle contact 64a, thereby protecting the first receptacle contact 64a. Furthermore, the inner peripheral wall 68 of the shutter 66 is arranged on the radially inner side of the second receptacle contact 64b to protect the second receptacle contact 64b.

As shown in FIG. 6 and FIG. 7, when connecting the plug 53 to the receptacle 54, the plug 53 is inserted into the receptacle 54. With the insertion of the plug 53 into the receptacle 54, the first and second drive surfaces 61a and 61b of the plug 53 sequentially come into contact with the release receiving surface 82 of the stopper 78 of the receptacle 54, and the first and second drive surfaces 61a and 61b sequentially press the release receiving surface 82 radially outwards, whereby the release receiving portion 81 of the stopper 78 is driven radially outwards. When the circumferential convex surface 77 of the stopper 78 is slid on the circumferential convex surface 76 of the partition wall portion 74, the stopper 78 is revolved from the regulating position to the releasing position, and the regulation convex portion 79 of the stopper 78 is removed from the regulation convex portion accommodation space 87 of the shutter 66. As a result, the regulation of the axially inward movement of the shutter 66 is released. It is to be noted that the release receiving portion 81 of the stopper 78 is accommodated in the notch portion 88 of the outer peripheral wall 69 of the shutter 66. Subsequently, the first and second drive surfaces 61a and 61b of the plug 53 abut on the first and second opening receiving surfaces 91a and 91b of the receptacle 54, respectively.

As shown in FIG. 7 and FIG. 8, the first and second opening receiving surfaces 91a and 91b of the receptacle 54 are pressed in the axially inward direction by the first and second drive surfaces 61a and 61b of the plug 53, respectively, and the shutter 66 is moved from the protecting position to the opening position in the axially inward direction against an axially outward compressing force of the shutter sustention member 73. The first sidewall portions 71a protecting the first receptacle contacts 64a are moved to the axially inner side apart from the first receptacle contacts 64a, and each entire first receptacle contact 64a protrudes axially outwards from the axially outer end opening between the two first sidewall portions 71a adjacent to each other. In this manner, the first receptacle contacts 64a are opened radially inwards. The inner peripheral wall 68 of the shutter 66 protecting the second receptacle contacts 64b is arranged on the axially inner side as compared with the second receptacle contact 64, each second receptacle contact 64b is arranged between the two adjacent first sidewall portions 71a protecting each first receptacle contact 64a, and the axially inner end portion of each second receptacle contact 64b protrudes radially inwards from the radially inner side opening between both the first sidewall portions 71a adjacent to each other. In this manner, each second receptacle contact 64b is opened radially inwards. When the second and first plug contacts 59b and 59a of the plug 53 are inserted to the radially inner side of the first and second receptacle contacts 64a and 64b, respectively, the first and second receptacle contacts 64a and 64b are brought into contact with the second and first plug contact 59b and 59a radially inwards, respectively. It is to be noted that the first and second receptacle contacts 64a and 64b are pressed radially inwards by the second and first plug contacts 59b and 59a, respectively, and they are displaced to and arranged on the radially inner side by elastic deformation of the first and second receptacle contacts 63a and 63b. Therefore, contact between the first and second receptacle contacts 64a and 64b and the second and first plug contacts 59b and 59a is assured by the elastic force of the first and second receptacle contacts 63a and 63b.

The electric connector according to the embodiment exercises the following effect.

Figure 9:
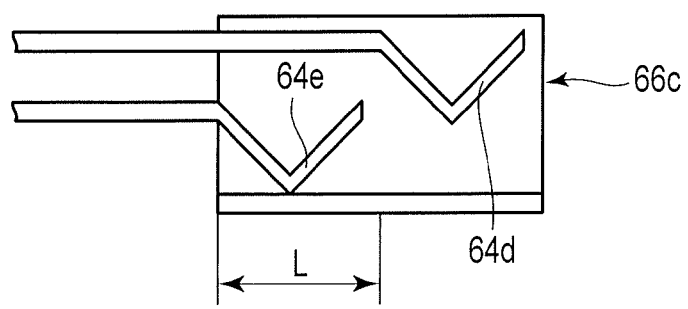
FIG. 9 is a schematic view showing a receptacle contact and a shutter according to a comparative example of the present invention.

In the receptacle 54 according to the embodiment, when the shutter 66 is arranged at the opening position by the first sidewall portions 71a in the shutter 66, the opening portion to open the second receptacle contacts 64*b* is formed. Here, as shown in FIG. 9, when the opening portion is not formed in a shutter 66*c*, the shutter 66*c* must be moved in the axially inward direction by a distance corresponding to the axial length of the first and second receptacle contacts 64*d* and 64*e* to open the first and second receptacle contacts 64*d* and 64*e* in the radially inward direction forming the opening direction. That is, the shutter 66*c* must be also be moved by a distance corresponding to an axial length L of the second receptacle contact 64*e*. On the other hand, in the receptacle 54 according to the embodiment, as shown in FIG. 5, the first and second receptacle contacts 64*a* and 64*b* can be opened in the opening direction by just moving the shutter 66 in the axially inward direction by the distance corresponding to the axial length of the first receptacle contact 64*a*, thereby reducing a moving distance of the shutter 66 in the axially inward direction. Therefore, the receptacle 54 can be minimized in the axial direction.

Additionally, each first sidewall portion 71*a* protecting the first receptacle contact 64*a* is arranged in such a manner that it does not overlap the second receptacle contact 64*b* when the shutter 66 is placed at the opening position as seen in the axial direction which is the moving direction of the shutter 66. Here, as shown in FIG. 10, when the first protecting portion which protects a first receptacle contact 64*g* is formed of, e.g., a peripheral wall 71*g* which is arranged to overlap a second receptacle contact 64*h* when a shutter 66*f* is placed at the opening position as seen in the axial direction which is the moving direction of the shutter 66*f*, the second receptacle contact 64*h* and the peripheral wall 71*g* cannot be arranged in an overlapping manner in the axial direction, and a space S1 that accommodates the peripheral wall 71*g* when the shutter 66*f* is placed at the opening position must be formed between the first receptacle contact 64*g* and the second receptacle contact 64*h* in the axial direction. On the other hand, in the receptacle 54 according to the embodiment, as shown in FIG. 5, the first receptacle contact 64*a* and the first sidewall portion 71*a* can be arranged to overlap each other in the axial direction, and a space which accommodates the first sidewall portion 71*a* when the shutter 66 is placed at the opening position does not have to be formed between the first receptacle contact 64*a* and the second receptacle contact 64*b* in the axial direction. Therefore, the first receptacle contact 64*a* and the second receptacle contact 64*b* can be arranged in close proximity to each other in the axial direction, and the receptacle 54 can be further minimized in the axial direction.

Furthermore, the first protecting portion which protects the first receptacle contact 64*a* is formed of the first sidewall portion 71*a* which is substantially parallel to the axial direction which is the moving direction of the shutter 66 and the radially inward direction which is the opening direction of the receptacle contacts 64*a* and 64*b*. Here, as shown in FIG. 11, when the first protecting portion which protects a first receptacle contact 64*j* is formed of, e.g., a peripheral wall 71*i* parallel to a moving direction of a shutter 66*i*, a space S2 which accommodates the peripheral wall 71*i* when the shutter 66*i* is placed at the opening position must be formed between the first receptacle contact 64*j* and a second receptacle contact 64*k*. On the other hand, in the embodiment, as shown in FIG. 5, a space which accommodates the first sidewall portion 71*a* when the shutter 66 is placed at the opening position does not have to be formed between the first receptacle contact 64*a* and the second receptacle contact 64*b* in the radial direction. Therefore, the first receptacle contact 64*a* and the second receptacle contact 64*b* can be arranged in close proximity to each other in the radial direction, and the receptacle 54 can be minimized in the radial direction.

Moreover, the second receptacle contact 64*b* is pressed in the radially inward direction by the inner peripheral wall 68 to be displaced radially outwards when the shutter 66 is arranged at the protecting position, and the radially outward pressing force applied to the second receptacle contact 64*b* by the inner peripheral wall 68 is released and the second receptacle contact 64*b* is restored to a natural position on the radially inner side when the shutter 66 is arranged at the opening position. Here, as shown in FIG. 12, when a second receptacle contact 64*n* and an inner peripheral wall 68*l* do not interact with each other and the second receptacle contact 64*n* is not displaced and restored in the radial direction, a space S3 must be formed between an outer peripheral surface of the inner peripheral wall 68*l* and a radially inner side surface of a first sidewall portion 71*m* in the radial direction forming an opening direction of receptacle contacts 64*m* and 64*n* to protrude a radially inner end portion of the second receptacle contact 64*n* radially outwards from a radially inner side opening between two first sidewall portions 71*m* adjacent to each other. On the other hand, in the embodiment, as shown in FIG. 5, a space does not have to be formed between the outer peripheral surface of the inner peripheral wall 68 and the radially inner side wall of the first sidewall portion 71*a*. Therefore, the receptacle 54 can be further minimized in the radial direction.

Additionally, when the plug 53 is inserted into the receptacle 54 and the first and second opening receiving surfaces 91*b* of the shutter 66 are pressed in the axially inward direction by the first and second drive surfaces 61*a* and 61*b* of the plug 53, the shutter 66 can be moved from the protecting position to the opening position in the axially inward direction against the axially outward compressing force of the shutter sustention member 73. As described above, since the moving distance of the shutter 66 in the axially inward direction is small, when moving the shutter 66 from the protecting position to the opening position in the axially inward direction, a compression amount of the compression member constituted of the elastic member is reduced, an increase in compressing force of the compression member is also decreased, and the pressing force required for moving the shutter 66 in the axially inward direction is reduced. Therefore, the plug 53 can be inserted into the receptacle 54 using relatively little force, and an operation of connecting the receptacle 54 to the plug 53 can be smoothly performed.

On the other hand, the first and second opening receiving surfaces 91*a* and 91*b* of the shutter 66 are inclined toward the radially inner side which forms the opening direction of the receptacle contacts 64*a* and 64*b* as seen in the axially inward direction which forms the moving direction of the shutter 66. Here, when the first and second opening receiving surfaces 91*b* are substantially orthogonal to the axial direction, even portions other than the first and second drive surfaces 61*a* and 61*b* in the plug 53 are apt to press the first and second opening receiving surfaces 91*b* in the axially inward direction. Therefore, the shutter 66 may be possibly accidentally moved from the protecting position to the opening position in the axially inward direction to open the receptacle contacts 64*a* and 64*b*.

In contrast, in the electric connector according to the embodiment, it is difficult for portions other than the first and second drive surfaces 61*a* and 61*b* in the plug 53 to press the first and second opening receiving surfaces 91*a* and 91*b*, thereby preventing the receptacle contacts 64*a* and 64*b* from being accidentally opened.

Further, the circumferential concave surface 76 of the partition wall portion 74 and the circumferential convex surface 77 of the stopper 78 in the receptacle housing 62 form a revolving mechanism of the stopper 78. Therefore, another member, such as a revolving shaft, does not have to be used in the revolving mechanism, and the revolving mechanism of the stopper 78 has a very simple configuration.

The electric connector can be used for a connecting portion between the universal cable 42 and the video processor 47, a connecting portion between the operation cable 49 and the operating section 50, and others besides the connecting portion between the insertion unit 32 and the drive unit 33.

Although the columnar plug and the cylindrical receptacle are used as the electric connector in the foregoing embodiment, the present invention can be applied to electrical connectors having any shape, and it can be applied to, e.g., an electric connector constituted of a plug formed into a rectangular column shape having electric contacts arranged on the entire circumference and a receptacle formed into a rectangular tubular shape or an electric connector constituted of a tabular plug having electric contacts arranged on one surface thereof and a receptacle formed into a rectangular tubular shape. Furthermore, although the moving direction of the shutter is parallel to the connecting direction of the electric connector in the foregoing embodiment, the present invention can be likewise applied to an electric connector in which a moving direction of a shutter is different from a connecting direction of the electric connector, and a moving direction of a shutter may be parallel to one surface and orthogonal to a connecting direction of an electric connector in the electrical connector constituted of a tabular plug having electric contacts arranged on the one surface and a receptacle having a rectangular tubular shape.

A reference invention of the present invention will now be described.

The reference invention relates to a liquid-tightness elastic member that enables insertion of a connecting portion extending from an outer surface portion of a device to the inside of the device, prevents a liquid from entering the inside from the outside of the device along the connecting portion, and holds the inside of the device in a liquid-tight manner with respect to the outside of the device.

Jpn. Pat. Appln. KOKAI Publication No. 2008-278971 discloses packing as a liquid-tightness elastic member. That is, an endoscope disclosed in Jpn. Pat. Appln. KOKAI Publication No. 2008-278971 is formed of an insertion portion which is inserted into a body cavity and a power unit which gives the insertion portion a driving force, and the insertion portion can be attached to or detached from the power unit. Moreover, an electric connector is formed at an attaching/detaching portion between the power unit and the insertion portion. In the insertion portion, an electric contact portion is arranged on an outer surface portion of a housing of a connector main body. A lead portion is extended to the inside of the insertion portion from the electric contact portion, and the lead portion pierces through the housing of the connector main body to protrude from a housing inner surface. The packing covers the housing inner surface, and the lead portion is inserted into the packing. The packing is pressed and crushed on the housing inner surface by a packing crushing member, thereby assuring water-tightness between the packing and the lead portion.

Jpn. Pat. Appln. KOKAI Publication No. 2008-278971 does not disclose a specific shape of the packing configured to assure the water-tightness between the packing and the lead portion at all.

In view of the above-described problem, it is an object of the reference invention to provide a liquid-tightness elastic member which can assuredly prevent a liquid from entering the inside from the outside of a device along a connecting portion and securely hold the inside of the device in a liquid-tight manner with respect to the outside of the device.

In one aspect of the reference invention, a liquid-tightness elastic member which holds the inside of a device in a liquid-tight manner with respect to the outside of the device includes: a pressing force receiving portion which is formed on an outer surface portion of the elastic member and can be pressed in a predetermined pressing direction; a support receiving portion which is formed on the outer surface portion of the elastic member and arranged to face the pressing force receiving portion in the pressing direction; an insertion hole which pierces the elastic member and extends between the pressing force receiving portion and the support receiving portion and in which a connecting portion extending from the outer surface portion of the device to the inside of the device can be inserted; an inclined portion which is formed on an inner peripheral portion of the insertion hole and inclined toward a contact direction which is substantially orthogonal to the pressing direction and is inward with respect to the insertion hole as seen in the pressing direction; an edge portion which is formed on the inner peripheral portion of the insertion hole, formed on the pressing direction side of the inclined portion, sharpened in the contact direction, and can come into contact with the connecting portion; and a protruding portion which is formed on the support receiving portion, protrudes in the pressing direction, and can be supported in a support direction which is an opposite direction of the pressing direction.

In the liquid-tightness elastic member according to this embodiment, the connecting portion extending from the outer surface portion of the device to the inside of the device is inserted into the insertion hole, the pressing force receiving portion is pressed in the pressing direction by a predetermined pressing portion, and the protruding portion is supported by a predetermined support portion in the support direction which is the opposite direction of the pressing direction. As a result, the elastic member is deformed, and the edge portion is firmly brought into contact with the connecting portion in the contact direction by functions of the inclined portion and the protruding portion in particular. Therefore, a liquid can be assuredly prevented from entering the inside from the outside of the device along the connecting portion, and the inside of the device can be securely held in the liquid-tight manner with respect to the outside of the device.

In a preferred embodiment of this reference invention, the liquid-tightness elastic member further includes a support direction regulation receiving portion which As formed on the support receiving portion, protrudes in the pressing direction, arranged on the opposite direction side of the contact direction with respect to the insertion hole, and can be supported in the support direction.

In the liquid-tightness elastic member according to this embodiment, the support direction regulation receiving portion is pressed in the pressing direction by the predetermined support portion, and the support direction regulation receiving portion is frictionally engaged with the support portion. As a result, movement of the support direction regulation receiving portion toward a relief direction, which is an opposite direction of a contact direction, is regulated, and a flow of the elastic member that moves the edge portion in the relief direction is reduced, thereby securely assuring firm contact of the edge portion and the connecting portion.

In a preferred embodiment of this reference invention, the liquid-tightness elastic member further includes a contact direction regulation receiving portion which is formed on an outer surface portion of the elastic member arranged on the opposite direction side of the contact direction and can be supported in the contact direction.

In the liquid-tightness elastic member according to this embodiment, the contact direction regulation receiving portion is supported in the contact direction by a predetermined regulating portion. As a result, movement of the support direction regulation receiving portion to the relief direction which is the opposite direction of the contact direction is regulated, and a flow of the elastic member that moves the edge portion in the relief direction is reduced, thereby securely assuring strong contact of the edge portion and the connecting portion.

In a preferred embodiment of this reference invention, the liquid-tightness elastic member further includes a relief portion which is formed on the outer surface portion of the elastic member arranged in the relief direction as the opposite direction of the contact direction and in which a flow space can be formed in the relief direction for the elastic member.

In the liquid-tightness elastic member according to this embodiment, the flow space is formed between a predetermined wall portion arranged on the relief direction side with respect to the elastic member and the relief portion, and a relief direction side portion of the elastic member is flowed into the flow space. As a result, deformation of the elastic member which moves the edge portion in the contact direction is facilitated, thereby securely assuring firm contact of the edge portion and the connecting portion.

In a preferred embodiment of this reference invention, the pressing force receiving portion can be arranged on the inner side of the device, the support receiving portion can be arranged on the outer surface portion side of the device, the connecting portion is an electric connecting portion, the elastic member includes the insertion holes and the protruding portions associated with the respective insertion holes, and the protruding portion is formed on the entire circumference of the corresponding insertion hole in the pressing direction.

In the liquid-tightness elastic member according to this embodiment, the support receiving portion of the elastic member is arranged on the outer surface portion side of the device, each electric connecting portion is inserted into each insertion hole, and each protruding portion is firmly brought into contact with a predetermined support portion. Each protruding portion is arranged on the entire circumference of each electric connecting portion, and each protruding portion is held in a liquid-tight manner with respect to the support portion, whereby the electric connecting portions are kept apart from each other in the liquid-tight manner. Therefore, the electric connecting portions are prevented from being short-circuited by a liquid that has entered the outer side of the edge portion along the connecting portions.

[Supplementary Note 1-1]

An electric connector portion includes first and second electric contact portions which are connectable to first and second target electric contact portions, respectively; and a protective member which is movable from a protecting position where the first and second electric contact portions are protected to an opening position where the first and second electric contact portions are opened in a moving direction extending from the first electric contact portion side to the second electric contact portion side, wherein the protective member includes an opening portion which is configured to open the second electric contact portion when the protective member is arranged at the opening position.

In the electrical connector portion according to the embodiment, since the opening portion to open the second electric contact portion is formed in the protective member, the first and second electric contact portions can be opened by just moving the protective member by the distance corresponding to the length of the first electric contact portion in the moving direction, thereby reducing the moving distance of the protective member. Therefore, the electric connector portion can be reduced in size in the moving direction of the protective member.

[Supplementary Note 1-2]

The second electric contact portion is arranged on an opening direction side of the first and second electric contact portions with respect to the first electric contact portion, the protective member includes a protective portion which is configured to protect the first electric contact portion when the protective member is arranged at the protecting position, and the protective portion includes the opening portion and is arranged in such a manner that it does not overlap the second electric contact portion as seen in the moving direction when the protective member is arranged at the opening position.

In the electric connector portion according to the embodiment, since the protective portion is arranged in such a manner that it does not overlap the second electric contact portion at the time that the protective member is arranged at the opening position as seen in the moving direction of the protective member, the second electric contact portion and the protective portion can be arranged in an overlapping manner in the moving direction of the protective member when the protective member is arranged at the opening position, and the space to accommodate the protective portion when the protective member is arranged at the opening position does not have to be provided between the first electric contact portion and the second electric contact portion in the moving direction of the protective member. Therefore, the first electric contact portion and the second electric contact portion can be arranged in close proximity to each other in the moving direction of the protective member, and the electric connector portion can be further reduced in size in the moving direction of the protective member.

[Supplementary Note 1-3]

The protective portion is formed of a sidewall portion which is substantially parallel to the moving direction and the opening direction.

In the electric connector portion according to the embodiment, since the protective portion is formed of a sidewall portion which is substantially parallel to the moving direction of the protective member and the opening direction of the electric contact portion, the space to accommodate the protective portion does not have be provided between the first electric contact portion and the second electric contact portion in the opening direction of the electric contact portion when the protective member is arranged at the opening position. Therefore, the first electric contact portion and the second electric contact portion can be arranged in close proximity to each other in the opening direction of the electric contact portion, and the electric connector portion can be reduced in size in the opening direction of the electric contact portion.

[Supplementary Note 1-4]

The electric connector portion is connectable to an target electric connector portion, the moving direction substantially coincides with a connecting direction of the target electric connector portion with respect to the electric connector portion, the protective member includes a driven portion which is pressed in the connecting direction by the target electric connector portion when connecting the target electric connector portion to the electric connector portion, and the driven portion is inclined toward the opening direction of the first and second electric contact portions in the connecting direction.

In the electric contact portion according to the embodiment, when connecting the target electric connector portion to the electric connector portion, the protective member is moved in the connecting direction by using the target electric connector portion to press the driven portion of the electric connector portion in the connecting direction of the target electric connector portion. Here, since the driven portion is inclined in the connecting direction of the protective member toward the opening direction of the electric contact portion, it is difficult for the driven portion to be pressed in the connecting direction by portions other than the target electric connector portion, thereby preventing accidentally moving the protective member to open the electric contact portion.

[Supplementary Note 1-5]

The electric connector portion further includes a housing portion onto which the protective member is movably provided; and a regulation member which is provided on the housing portion, has an end portion, and is configured to revolve about the end portion between a regulating position where movement of the protective member is regulated and a releasing position where movement of the protective member is enabled, wherein the regulation member includes a slide convex portion provided at the end portion, and the housing portion includes a slide concave portion which is configured to slidably support the slide convex portion to enable revolution of the regulation member about the end portion between the regulating position and the releasing position.

In the electric connector portion according to the embodiment, the slide concave portion of the housing portion and the slide convex portion at the end portion of the regulation member form the revolving mechanism, and the revolving mechanism of the revolving member has a very simple configuration.

[One Embodiment of Reference Invention]

One embodiment of the reference invention will now be described with reference to the drawings.

The one embodiment of the reference invention will now be explained with reference to FIG. 1 and FIG. 13 to FIG. 18.

Referring to FIG. 1, an endoscopic system according to the one embodiment of the reference invention has the same configuration as that of the endoscopic system according to the embodiment of the present invention.

A plug 53 according to the one embodiment of the reference invention will now be described in detail with reference to FIG. 13 to FIG. 18.

Figure 13:
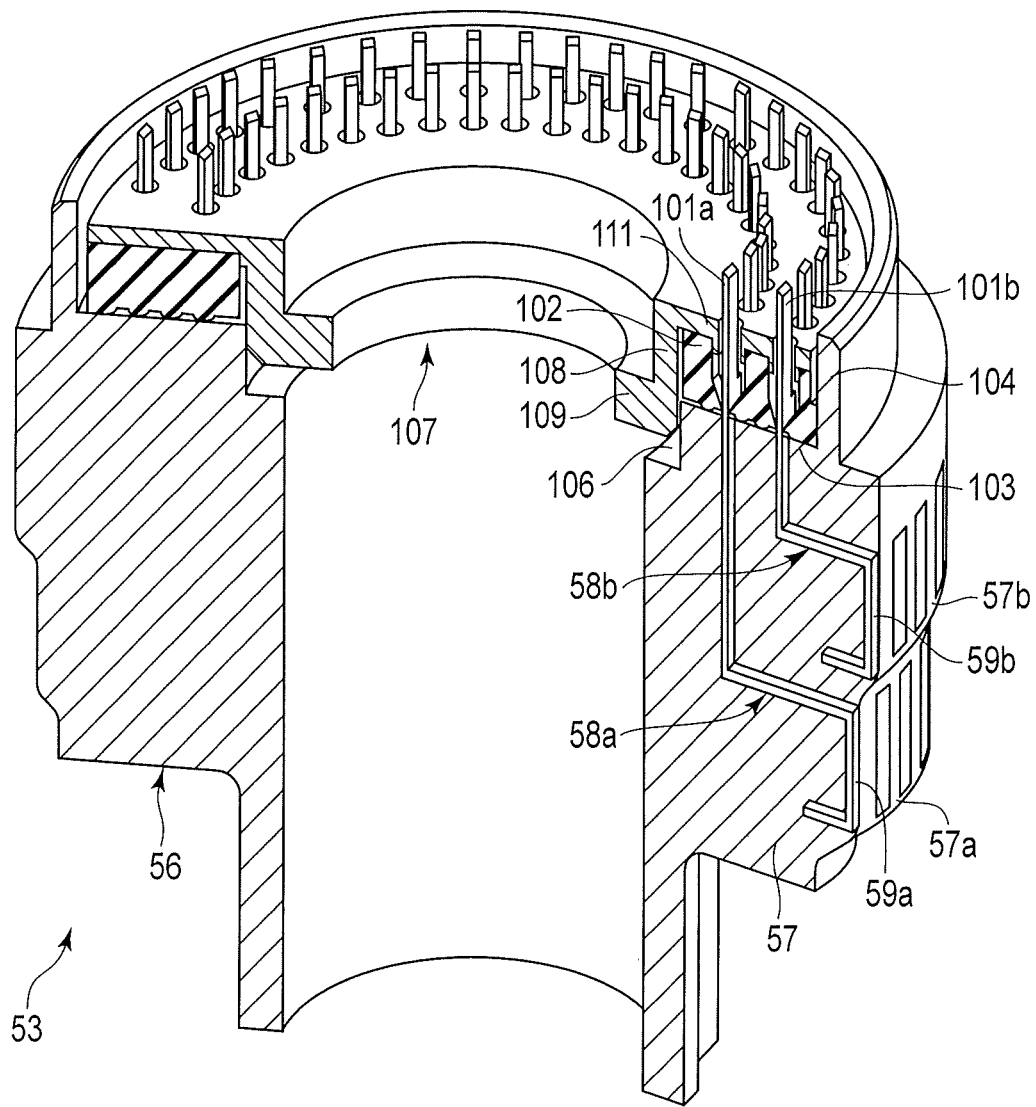
FIG. 13 is a partially longitudinal cross-sectional perspective view showing an electric connector according to an embodiment of a reference invention of the present invention.

Referring to FIG. 13, the plug 53 according to the one embodiment of the reference invention has the same configuration as that of the plug 53 according to the embodiment of the present invention.

Further, each of plug contacts 58a and 58b as electric connecting portions has a rectangular cross section orthogonal to a longitudinal direction of the plug contacts 58a and 58b. Further, first and second lead portions 101a and 101b are formed of axially inner end portions of the first and second plug contacts 58a and 58b, respectively. Many first and second lead portions 101a and 101b protrude in an axially inward direction from an axially inner end surface of a plug housing 56. Many first lead portions 101a and many second lead portions 101b are provided in parallel in a circumferential direction, respectively, and each corresponding second lead portion 101b is arranged on the radially outer side of each first lead portion 101a. A pair of opposed side surfaces of the lead portions 101a and 101b are arranged to be orthogonal to the radial direction.

Moreover, a liquid-tight mechanism which prevents a liquid from entering the inside from the outside of an insertion unit 32 along the plug contacts 58a and 58b and holds the inside in a liquid-tight manner with respect to the outside of the insertion unit 32 is formed in the plug 53 according to the one embodiment of the reference invention.

The liquid-tight mechanism will now be described in detail with reference to FIG. 13 to FIG. 17.

It is to be noted that each drawing shows a situation that packing 102 as a liquid-tightness elastic member is in a non-pressed state.

Figure 14:
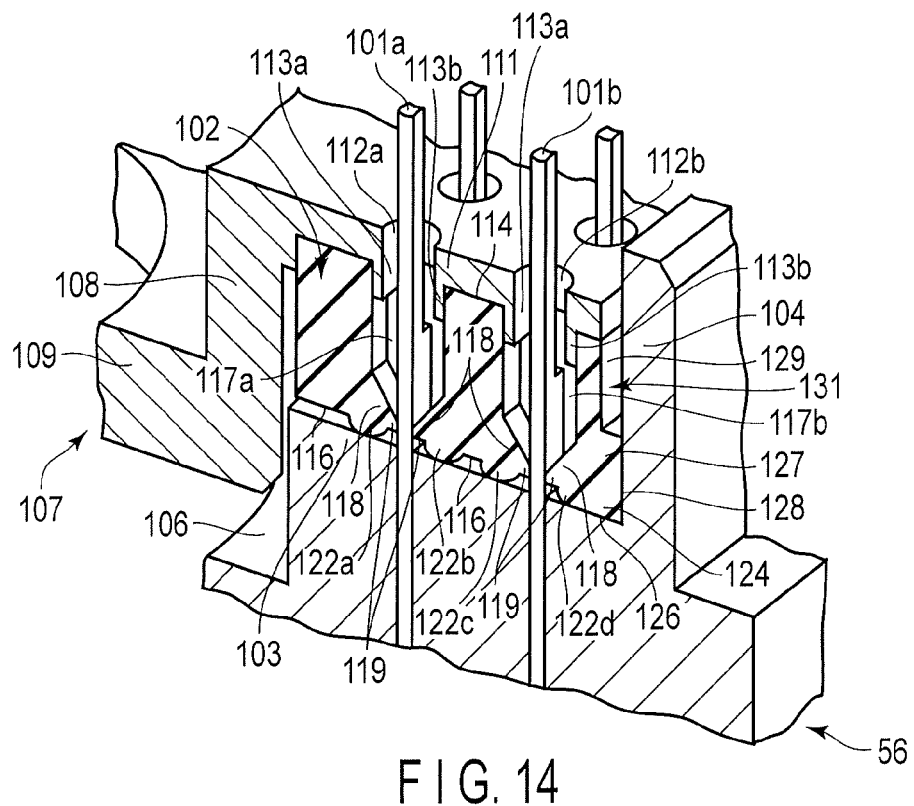
FIG. 14 is a partially longitudinal cross-sectional enlarged perspective view showing the electric connector according to the embodiment of the reference invention of the present invention.
Figure 15:
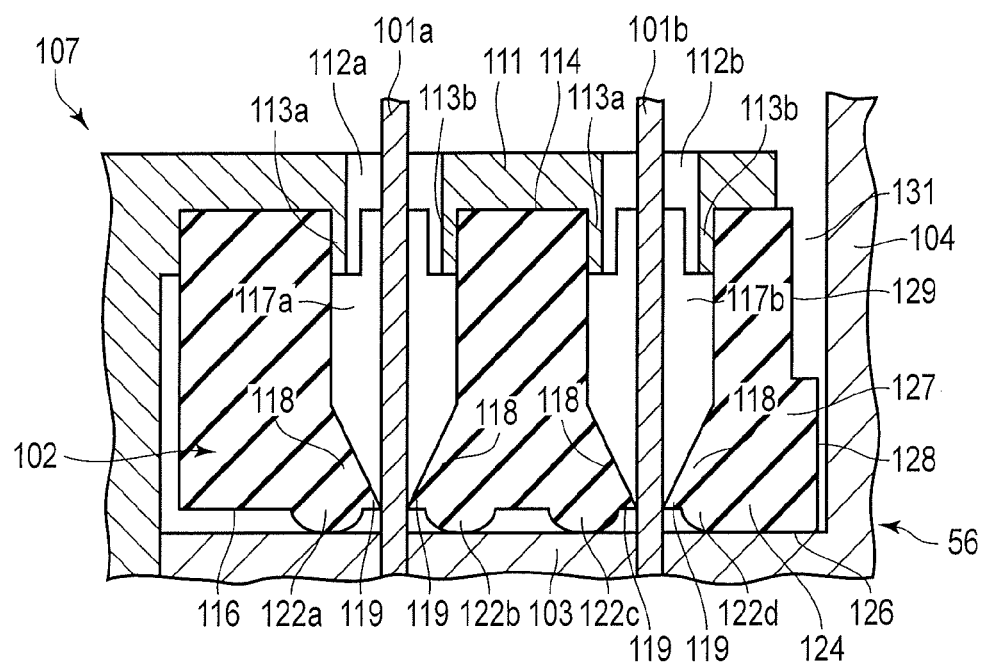
FIG. 15 is a longitudinal cross-sectional view showing the electric connector according to the embodiment of the reference invention of the present invention.
Figure 16:
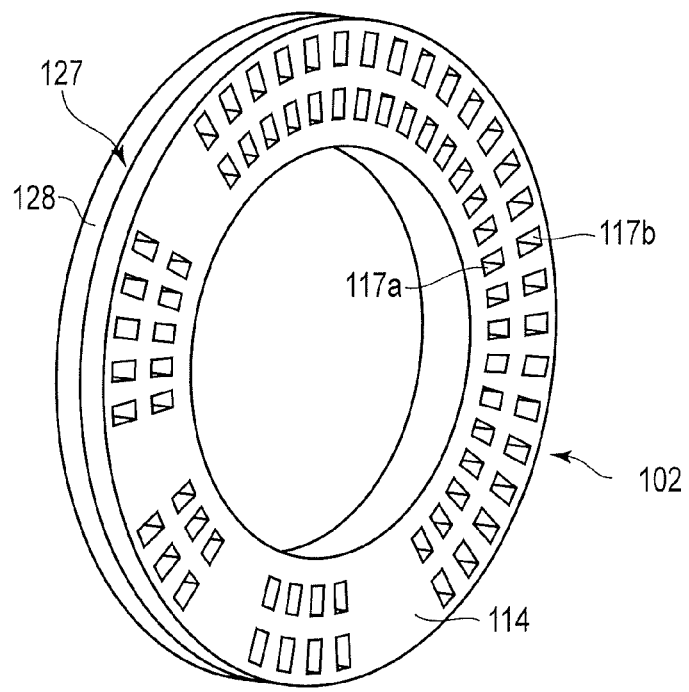
FIG. 16 is a perspective view showing the packing according to the embodiment of the reference invention of the present invention from a pressing force receiving surface side.
Figure 17:
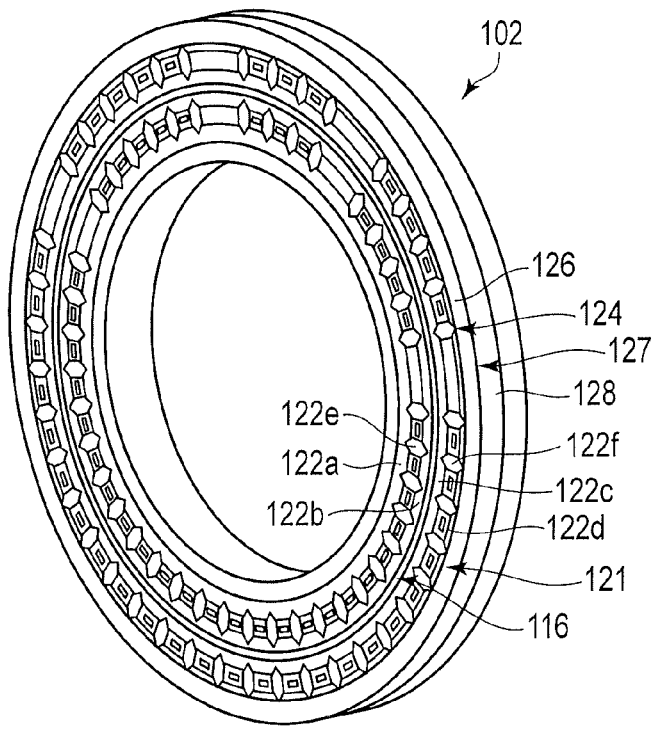
FIG. 17 is a perspective view showing the packing according to the embodiment of the reference invention of the present invention from a support receiving surface side.

Referring to FIG. 13 to FIG. 15, a support wall 103 as a support portion is formed of the axially inner end surface of the plug housing 56. A cylindrical regulation sidewall 104 as a regulating portion and a wall portion is provided at a radially outer edge portion on the axially inner end surface of the plug housing 56 to protrude to the axially inward direction. A large-inside-diameter portion having an increased inside diameter is formed at the axially inner end of the plug housing 56, and a slide receiving portion 106 is formed of the large-inside-diameter portion.

A pressing member 107 is provided to cover the axially inner end portion of the plug housing 56. A cylindrical slide portion 108 is formed in the pressing member 107. The slide portion 108 is interpolated into the slide receiving portion 106 of the plug housing 56 from the axially inner side, and it can slide in the axial direction with respect to the slide receiving portion 106. An annular thick plate-like elastic load receiving portion 109 which protrudes in the radially inward direction and extends over the entire circumference is formed on the axially outer end portion of the slide portion 108. The elastic load receiving portion 109 can be compressed in the axially outward direction with respect to the plug housing 56, and the entire pressing member 107 can be compressed in the axially outward direction with respect to the plug housing 56. On the other hand, an annular thin plate-like pressing wall 111 which protrudes in the radially outward direction and extends over the entire circumference is formed as a pressing portion on the axially inner end portion of the slide portion 108. The pressing wall 111 is arranged on the axially inner side of the support wall 103 to face the support wall 103 of the plug housing 56, and it is also arranged on the radially inner side of the regulation sidewall 104 of the plug housing 56. Many first and second insertion openings 112a and 112b are formed to pierce the pressing wall 111 in the axial direction. A transverse section of each of the insertion openings 112a and 112b orthogonal to the axial direction has a circular shape. Many first insertion openings 112a and many second insertion openings 112b are aligned in the circumferential direction, respectively, and a corresponding second insertion opening 112b is arranged on the radially outer side of a first insertion opening 112a. Each corresponding first or second lead portion 101a or 101b is inserted into each first or second insertion opening 112a or 112b. Additionally, a pair of tongue pieces 113a and 113b are provided on the axially outer end surface of the pressing wall 111 to protrude in the axially outward direction around the respective insertion openings 112a and 112b. Each of the tongue pieces 113a and 113b has a circular peripheral wall shape extending in the circumferential direction of each of the insertion openings 112a and 112b, and in the pair of tongue pieces 113a and 113b, one tongue piece 113a is arranged on the radially inner side with respect to each of the insertion openings 112a and 112b and the other tongue piece 113b is arranged on the radially outer side with respect to each of the insertion openings 112a and 112b.

Referring to FIG. 14 to FIG. 17, the packing 102 is arranged between the plug housing 56 and the pressing member 107. The packing 102 has an annular thick plate-like shape, and it is made of an elastic material such as silicone rubber, butyl rubber, elastomer, or natural rubber.

An axially inner end surface of the packing 102 forms a pressing force receiving surface 114 as a pressing force receiving portion. The pressing force receiving surface 114 is arranged to face the pressing wall 111 of the pressing member 107, and it can be pressed to the axially outward pressing direction by the pressing wall 111. Further, an axially outer end surface of the packing 102 forms a support receiving surface 116 as a support receiving portion.

Many first and second insertion holes 117a and 117b are formed to axially pierce the packing 102 between the pressing force receiving surface 114 and the support receiving surface 116. Many first insertion holes 117a and many second insertion holes 117b are aligned in the circumferential direction, respectively, and a corresponding second insertion hole 117b is arranged on the radially outer side of each first insertion hole 117a. An axially inner end opening portion of each first or second insertion hole 117a or 117b is arranged to face each corresponding first or second insertion opening 112a or 112b of the pressing wall 111. Furthermore, a pair of tongue pieces 113a and 113b around each corresponding first or second insertion opening 112a or 112b are inserted into the axially inner end opening portion of each first or second insertion hole 117a or 117b. Moreover, each corresponding first or second lead portion 101a or 101b is inserted into each first or second insertion hole 117a or 117b. A transverse cross section of each of the insertion holes 117a and 117b orthogonal to the axial direction has a rectangular shape, and a pair of opposed side surfaces of each of the insertion holes 117a and 117b are arranged to be orthogonal to the radial direction, thereby forming a radially inner side surface and a radially outer side surface.

A flat surface portion is formed on an axially inner side portion of each of the radially inner side surface portion and the radially outer side surface portion of the insertion hole 117a or 117b, and an inclined portion 118 is formed on an axially outer side portion of the same. In the radially inner side surface portion of each of the insertion holes 117a and 117b, the inclined portion 118 has a tapered shape which is inclined toward a radially outward contact direction as seen in the axially outward pressing direction. An edge portion 119 having an edge shape which is sharpened toward the radially outward contact direction is formed at an axially outer end portion of the inclined portion 118, and the edge portion 119 is brought into contact with each of the lead portions 101a and 101b in the contact direction. In the one embodiment of the reference invention, the inclined portion 118 extends to an axially outer end of each of the insertion holes 117a and 117b, and the edge portion 119 is arranged at the axially outer end of each of the insertion holes 117a and 117b. The edge portion 119 is formed of an inclined surface of the inclined portion 118 and the support receiving surface 116. The same inclined portion 118 and the edge portion 119 are likewise formed on the radially outer side surface portion of each of the insertion holes 117a and 117b. However, the inclined portion 118 has a tapered shape which is inclined toward the radially inward contact direction as seen in the axially outward pressing direction, and the edge portion 119 has an edge shape sharpened in the radially inward contact direction. Each of the lead portions 101a and 101b is held by the pair of edge portions 119, and the pair of edge portions 119 are brought into contact with the entire circumference of each of the lead portions 101a and 101b.

A ridge portion 121 as a protruding portion is formed on the support receiving surface 116 of the packing 102. The ridge portion 121 protrudes in the axially outward pressing direction. The ridge portion 121 includes a plurality of ridge portions. That is, first to fourth annular ridge portions 122a, 122b, 122c, and 122d extend over the entire circumference, and they are aligned in the radial direction. The first and second annular ridge portions 122a and 122b are arranged on the radially inner side and outer side with respect to the first insertion hole 117a, respectively, and they are brought into line in the axial direction with respect to the radially inner side surface and outer side surface of the first insertion hole 117a. Further, the third and fourth annular ridge portions 122c and 122d are arranged on the radially inner side and outer side with respect to the second insertion hole 117b, respectively, and they are brought into line in the axial direction with respect to the radially inner side surface and outer side surface of the second insertion hole 117b. A cross section of each of the first to third annular ridge portions 122a, 122b, and 122c orthogonal to the circumferential direction has a convex semicircular shape in the axially outward direction, and a cross section of the fourth annular ridge portion 122d orthogonal to the circumferential direction is formed of a semicircular radially inner side portion protruding in the axially outward direction. Furthermore, many first radial ridge portions 122e radially extend between the first annular ridge portion 122a and the second annular ridge portion 122b, and they are aligned in the circumferential direction and continuous with the first and second annular ridge portions 122a and 122b. Moreover, many second radial ridge portions 122f radially extend between the third annular ridge portion 122c and the fourth annular ridge portion 122d, and they are aligned in the circumferential direction and continuous with the third and fourth peripheral ridge portions 122c and 122d. A cross section of each of the first and second radial ridge portions 122e and 122f orthogonal to the radial direction has a semicircular shape protruding in the axially outward direction. The ridge portion 121 is supported by the support wall 103 of the plug housing 56 in an axially inward support direction which is an opposite direction of the pressing direction.

Additionally, as seen in the axially outward pressing direction, the first lead portion 101a is surrounded by the first and second peripheral ridge portions 122a and 122b and the two first radial ridge portions 122e adjacent to each other in the circumferential direction. Further, the second lead portion 101b is surrounded by the third and fourth peripheral ridge portions 122c and 122d and the two second radial ridge portions 122f adjacent to each other in the circumferential direction. In other words, as seen in the axially outward pressing direction, the ridge portion 121 is formed over the entire circumference of each lead portion 101a or 101b.

A regulation base portion 124 as a support direction regulation receiving portion is formed on the support receiving surface 116 of the packing 102. The regulation base portion 124 protrudes in the axially outward pressing direction, is arranged on a radially outer edge portion of the support receiving surface 116, extends over the entire circumference, and formed on the radially outer side of the fourth peripheral ridge portion 122d to be integral with the fourth peripheral ridge portion 122d. Here, a contact direction of the edge portion 119 on the radially outer side surface portion of the second insertion hole 117b is a radially inward direction, and a radially outward direction which is an opposite direction of the contact direction is a relief direction. The regulation base portion 124 is arranged on the relief direction side with respect to the second insertion hole 117b. Further, a cross section of the regulation base portion 124 orthogonal to the circumferential direction has a rectangular shape protruding in the axially outward direction. A regulation end surface 126 substantially orthogonal to the axial direction is formed at a protruding end portion of the regulation base portion 124. The regulation end surface 126 is supported in the axially inward direction as the support direction by the support wall 103 of the plug housing 56, and it is frictionally engaged with the support wall 103. The frictional engagement of the regulation end surface 126 and the support wall 103 regulates movement of the regulation base portion 124 in the radially outward relief direction.

A regulation bulge portion 127 as a contact direction regulation receiving portion is formed on an axially outer side part of the outer peripheral portion of the packing 102. In the packing 102, the regulation bulge portion 127 is formed on the outer surface portion arranged on the radially outward relief direction side. The regulation bulge portion 127 bulges in the radially outward relief direction and extends over the entire circumference. A cross section of the regulation bulge portion 127 orthogonal to the circumferential direction has a rectangular shape protruding in the radially outward direction. A regulation side surface 128 which is substantially orthogonal to the radial direction is formed on a bulge end portion of the regulation bulge portion 127. The regulation side surface 128 is supported in the radially inward contact direction by the regulation sidewall 104 of the plug housing 56, and movement of the regulation bulge portion 127 in the radially outward relief direction is regulated.

A relief surface 129 as a flank portion is formed on an axially inner side part of the outer peripheral portion of the packing 102. In the packing 102, the relief surface 129 is formed on the outer surface portion arranged on the radially outward relief direction side. The regulation sidewall 104 of the plug housing 56 is arranged on the radially outward relief direction side with respect to the packing 102, and a flow space 131 is formed between the relief surface 129 and the regulation sidewall 104.

A pressed state of the packing 102 will now be described hereinafter.

The pressing member 107 is arranged and fixed at a pressing position on the axially outer side with respect to the plug housing 56. The pressing force receiving surface 114 of the packing 102 is pressed in the axially outward pressing direction by the pressing wall 111 of the pressing member 107. Further, the ridge portion 121 of the packing 102 is supported in the axially inward direction which is the support direction by the support wall 103 of the plug housing 56. The entire packing 102 is deformed to compress in the axial direction and deformed to expand in the radial direction.

Figure 18:
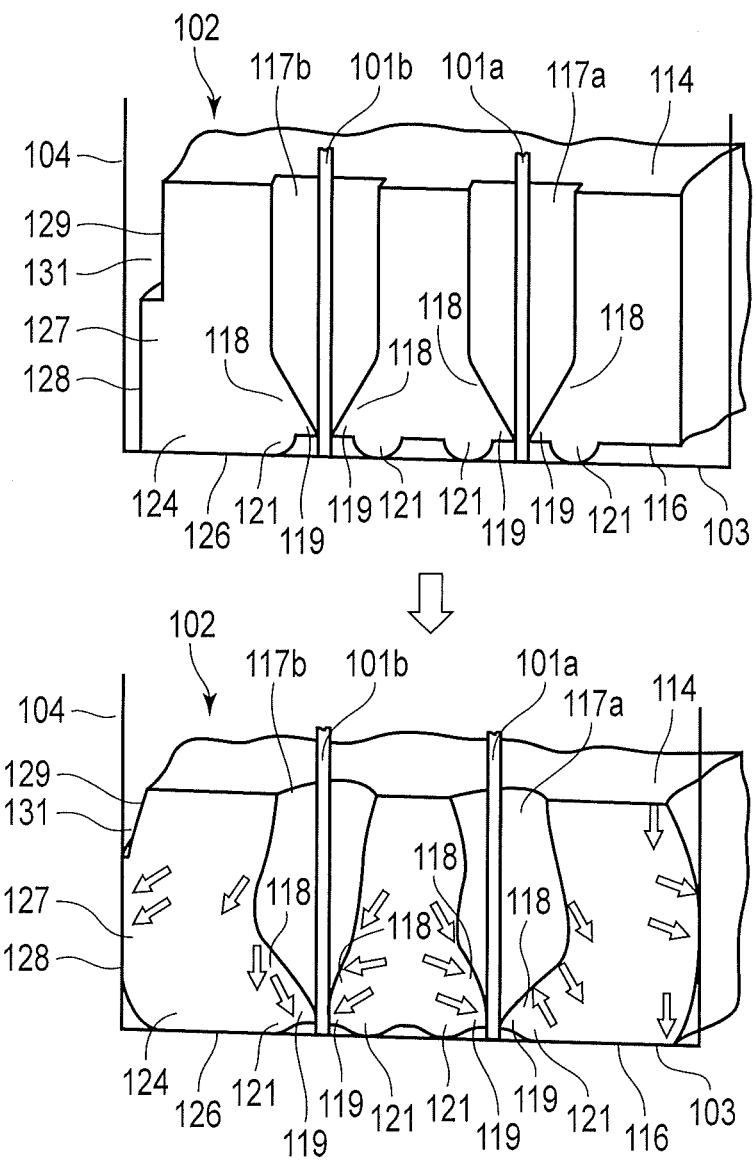
FIG. 18 is a schematic view showing a modification of the packing according to the embodiment of the reference invention of the present invention.

A deformed state of each of the insertion holes 117a and 117b on the radial side surface portion will now be described in detail with reference to FIG. 18.

The deformed state of each of the insertion holes 117a and 117b on the radial side surface portion differs depending on whether the radial side surface portion is arranged in the packing 102 or whether the same is arranged near the outside of the packing 102, and the deformed state differs depending on whether the regulation base portion 124 or the regulation bulge portion 127 is formed on the outer side of the radial side surface portion if the radial side surface portion is arranged near the outside of the packing 102.

The radially outer side surface portion of the first insertion hole 117a is arranged in the packing 102. In the vicinity of the flat surface portion of the axially outer side portion, a stress vector mainly faces the axially outward pressing direction side, and it is inclined toward the radially inward contact direction at a relatively small inclination angle with respect to the pressing direction. On the other hand, in the inclined portion 118, a stress vector mainly faces the radially inward contact direction side, and it is inclined toward the axially outward pressing direction at a relatively small inclination angle with respect to the contact direction. However, the inclination angle is gradually increased from the axially inner side toward the axially outer side. The ridge portion 121 assures a gap between the support wall 103 and the edge portion 119, a stress vector mainly faces the radially inward contact direction side near the edge portion 119, and hence the edge portion 119 is strongly brought into contact with the lead portion 101a in the radially inward contact direction.

The radially inner side surface portion of the second insertion hole 117b is also arranged in the packing 102. A deformed state of the radially inner side surface portion of the second insertion hole 117b is the same as the deformed state of the radially outer side surface portion of the first insertion hole 117a. However, the contact direction is the radially outward direction in the radially inner side surface portion of the second insertion hole 117b, and a stress vector in the radially inner side surface portion of the second insertion hole 117b is opposite to the stress vector in the radially outer side surface portion of the first insertion hole 117 in regard to the radial direction. The edge portion of the radially inner side surface portion of the second insertion hole 117b is strongly brought into contact with the lead portion 101b in the radially outward contact direction.

The radially inner side surface portion of the first insertion hole 117a is arranged near the outside of the packing 102, and neither the regulation base portion 124 nor the regulation bulge portion 127 is formed on the outer side. Therefore, the outer side portion, i.e., the radially inner side portion of the packing 102 with respect to the radially inner side surface portion of the first insertion hole 117 is flowed in the axially outer pressing direction and the radially inward relief direction as a whole. However, since the packing 102 according to the one embodiment of the reference invention has an annular shape, the flow of the packing 102 is relatively small at the radially inner side portion of the packing 102. In the flat surface portion and in the vicinity of the axially inner side portion of the inclined portion 118, a stress vector mainly faces the axially outward pressing direction side, and it is inclined toward the radially inward relief direction with respect to the pressing direction at a relatively small inclination angle. In the vicinity of the axially outer side portion of the inclined portion 118, a stress vector is inclined toward the axially inward support direction at a relatively large inclination angle with respect to the radially outward contact direction. That is, in the vicinity of the edge portion 119, the stress vector is inclined toward the axially inward support direction at the relatively large inclination angle with respect to the radially outward contact direction, and hence the contact force of the edge portion 119 with respect to the lead portion 101a is slightly reduced. However, as described above, since the flow of the packing 102 is relatively small at the radially inner side portion of the packing 102, a reduction in contact force is relatively small, and the necessary contact force is assured.

The radially outer side surface portion of the second insertion hole 117b is arranged near the outside of the packing 102, and the regulation base portion 124 and the regulation bulge portion 127 are formed on the outer side. The outer side portion, i.e., the radially outer side portion of the packing 102 for the radially outer side surface portion of the second insertion hole 117b is flowed in the radially outward relief direction as a whole. However, since the regulation base portion 124 is pressed against the support wall 103 in the axially outward pressing direction and the regulation end surface 126 of the regulation base portion 124 is strongly frictionally engaged with the support wall 103, movement of the regulation base portion 124 in the radially outward relief direction is regulated. Further, since the regulation bulge portion 127 is supported by the regulation sidewall 104 in the radially inward contact direction, movement of the regulation sidewall 104 in the radially outward relief direction is regulated. Therefore, the flow of the packing 102 in the radially outward relief direction is reduced. In the radially outer side surface portion of the second insertion hole 117b, a stress vector mainly faces the axially outward pressing direction side in the flat surface portion and in the vicinity of the axially inner side part of the inclined portion 118, and it is inclined toward the radially outward relief direction at a relatively small inclination angle. In the vicinity of the axially outer side part of the inclined portion 118, a stress vector is inclined toward the axially outward pressing direction at a relatively large inclination angle with respect to the radially inward contact direction. That is, in the vicinity of the edge portion 119, the stress vector is inclined toward the axially outward pressing direction at a relatively large inclination angle with respect to the radially inward contact direction, and hence the contact force of the edge portion 119 with respect to the lead portion 101b is slightly reduced. However, as described above, since the flow of the packing 102 in the radially outward relief direction is reduced by the regulation base portion 124 and the regulation bulge portion 127, the reduction in contact force is relatively small, and the necessary contact force is assured.

It is to be noted that the flow space 131 is formed between the relief surface 129 of the packing 102 and the regulation sidewall 104 of the plug housing 56 in the non-pressed state of the packing 102. Here, in the packing 102 that the flow space 131 is not formed in the non-pressed state, it is difficult for the outer peripheral portion of the packing 102 to flow in the radially outward direction by pressing the packing 102, thus a compressing function of the packing 102 itself is increased in the pressed state, but a deforming function that brings the edge portion 119 into contact with the packing 102 is not facilitated very much. On the other hand, in the one embodiment of the reference invention, since the outer peripheral portion of the packing 102 is flowed into the flow space 131 by pressing the packing 102, the deforming function that brings the edge portion 119 into contact with the packing 102 in the pressed state can be sufficiently facilitated.

A liquid-tight function of the packing 102 will now be described.

There is a possibility that a liquid enters and reaches the lead portions 101a and 101b from the plug contacts 59a and 59b on the outer surface portion of the plug housing 56 along the plug contacts 58a and 58b through the gaps between the plug housing 56 and the plug contacts 58a and 58b. In particular, when the plug housing 56 and the plug contacts 58a and 58b are integrally formed by insert molding, gaps may be possibly formed between the plug housing 56 and the plug contacts 58a and 58b by interface delamination, thus continued water-tightness cannot be assured.

In the one embodiment of the reference invention, each of the lead portions 101a and 101b is held between the pair of edge portions 119, the pair of edge portions 119 are strongly brought into contact with the entire circumference of the lead, and liquid-tightness between the pair of edge portions 119 and the lead portion 101a or 101b is assured. Therefore, even if a liquid has entered to reach the lead portions 101a and 101b, the liquid does not enter the insertion unit 32 along the plug contacts 58a and 58b across the edge portions 119, and liquid-tightness in the insertion unit 32 is maintained with respect to the outside.

Further, the ridge portion 121 of the packing 102 is arranged over the entire circumference of each of the lead portions 101a and 101b, and the protruding end portion of the ridge portion 121 is strongly brought into contact with the support wall 103 of the plug housing 56 to assure the liquid-tightness between the protruding end portion of the ridge portion 121 and the support wall 103 in the pressed state of the packing 102. That is, the lead portions 101a and 101b are kept apart from each other in the liquid-tight manner. Although the liquid that has flowed to the lead portions 101a and 101b is prevented from entering the inside by the edge portions 119 and the liquid stays on the outer side of the edge portions 119, the lead portions 101a and 101b are kept apart from each other in the liquid-tight manner, and hence the lead portions 101a and 101b are not short-circuited by this liquid.

The plug 53 according to the one embodiment of the reference invention exercises the following effects.

In the plug 53 according to the one embodiment of the reference invention, the entire packing 102 is deformed to compress in the axial direction and deformed to expand in the radial direction, and the edge portions 119 are strongly brought into contact with the lead portions 101a and 101b of the plug contacts 58a and 58b in the radially outward or radially inward contact direction by functions of the inclined portions 118 and the ridge portion 121 in particular. Therefore, the liquid is assuredly prevented from entering the inside from the outside of the insertion unit 32 along the plug contacts 58a and 58b, and the liquid-tightness in the insertion unit 32 can be securely maintained with respect to the outside.

In particular, the regulation base portion 124 of the packing 102 is pressed by the support wall 103 of the connector housing in the axially outward pressing direction and frictionally engaged with the support wall 103, and hence movement of the regulation base portion 124 in the radially outward relief direction is regulated. Furthermore, the regulation bulge portion 127 of the packing 102 is supported in the radially inward direction by the regulation sidewall 104 of the plug housing 56, and movement of the regulation bulge portion 127 in the radially outward relief direction is regulated. Therefore, the flow of the packing 102 that moves the edge portion 119 of the radially outer side surface portion of the second insertion hole 117b in the radially outward relief direction is reduced. Therefore, firm contact between the edge portion 119 of the radially outer side surface portion of the second insertion hole 117b and the lead portion 101b of the plug contact 58b is assured.

It is to be noted that the flow space 131 is formed between the relief surface 129 of the packing 102 and the regulation sidewall 104 of the plug housing 56 in the non-pressed state of the packing 102, and the outer peripheral portion of the packing 102 is flowed toward the flow space 131 in the radially outward direction in the pressed state of the packing 102. As a result, deformation of the packing 102 that moves the edge portion 119 of the radially outer side surface portion of the second insertion hole 117b in the radially inward contact direction is facilitated.

Moreover, the ridge portion 121 is arranged over the entire circumference of each plug contact 58a or 58b, and the protruding end portion of the ridge portion 121 is strongly brought into contact with the support wall 103 of the plug housing 56, thereby maintaining the liquid-tightness between the ridge portion 121 and the support wall 103. As a result, the lead portions 101a and 101b are kept apart from each other in the liquid-tight manner. Therefore, the liquid that has entered and reaches the outer side of the edge portions 119 along the plug contacts 58a and 58b is prevented from causing short-circuit of the plug contacts 58a and 58b.

The above-described packing 102 can be used for the receptacle 54 of the drive unit 33, the plug and the receptacle of the connector that connects the universal cable 42 to the video processor 47, and the plug and the receptacle of the connector connecting the operation cable 49 to the operating section 50 besides the plug 53 of the insertion unit 32.

[Supplementary Note 2-1]

A liquid-tightness elastic member (102) which maintains liquid-tightness in a device (32) with respect to the outside of the device (32), comprising:

a pressing force receiving portion (114) which is formed on an outer surface portion of the elastic member (102) and configured to be pressed in a predetermined pressing direction;

a support receiving portion (116) which is formed on the outer surface portion of the elastic member (102) and arranged to face the pressing force receiving portion (114) in the pressing direction;

an insertion hole (117a; 117b) which is configured to pierce the elastic member (102), extend between the pressing force receiving portion (114) and the support receiving portion (116), and allow a connecting portion (58a; 58b) extending from an outer surface portion of the device (32) to the inside of the device (32) to be inserted therethrough;

an inclined portion (118) which is formed on an inner peripheral portion of the insertion hole (117a; 117b) and inclined toward a contact direction which is substantially orthogonal to the pressing direction and is inward with respect to the insertion hole (117a; 117b) as seen in the pressing direction;

an edge portion (119) which is formed on the inner peripheral portion of the insertion hole (117a; 117b), formed on the pressing direction side of the inclined portion (118), sharpened in the contact direction, and configured to be brought into contact with the connecting portion (58a; 58b); and a protruding portion (121) which is formed on the support receiving portion (116), configured to protrude in the pressing direction, and configured to be supported in a support direction which is opposite to the pressing direction.

[Supplementary Note 2-2]

The liquid-tightness elastic member according to Supplementary Note 2-1, further comprising:

a support direction regulation receiving portion (124) which is formed on the support receiving portion (116), which is configured to protrude in the pressing direction, which is arranged on the opposite direction side of the contact direction with respect to the insertion hole (117a; 117b), and which is configured to be supported in the support direction.

[Supplementary Note 2-3]

The liquid-tightness elastic member according to Supplementary Note 2-1, further comprising:

a contact direction regulation receiving portion (127) which is formed on the outer surface portion of the elastic member (102) on the opposite direction side of the contact direction and configured to be supported in the contact direction.

[Supplementary Note 2-4]

The liquid-tightness elastic member according to Supplementary Note 2-1, further comprising:

a relief portion (129) which is formed on the outer surface portion of the elastic member (102) arranged on a relief direction side as an opposite direction of the contact direction and configured to form a flow space (131) in the relief direction side with respect to the elastic member (102).

[Supplementary Note 2-5]

The liquid-tightness elastic member according to Supplementary Note 2-1, wherein:

the pressing force receiving portion (114) is able to be arranged on the inner side of the device (32), the support receiving portion (116) is able to be arranged on the outer surface portion side of the device (32), the connecting portion (58a; 58b) is an electric connecting portion (58a; 58b), the elastic member (102) includes the insertion holes (117a; 117b) and the protruding portions (121) associated with the respective insertion holes (117a; 117b), and the protruding portion (121) is formed over the entire circumference of the corresponding insertion hole (117a; 117b) as seen in the pressing direction.

[Supplementary Note 2-6]

A connector portion comprising: the elastic member (102) described in Supplementary Note 2-1;

a pressing portion (111) which is configured to press the pressing force receiving portion (114) in the pressing direction;

a connecting portion (58a; 58b) which extends from the outer surface portion of the device (32) to the inside of the device (32) to be inserted into the insertion hole (117a; 117b); and a support portion (103) which supports the protruding portion (121) in the support direction.

[Supplementary Note 2-7]

The connector portion according to Supplementary Note 2-6, wherein:

the elastic member (102) includes a support direction regulation receiving portion (124) which is formed on the support receiving portion (116), which is configured to protrude in the pressing direction, which is arranged on the opposite direction side of the contact direction with respect to the insertion hole (117a; 117b), and which is configured to be supported in the support direction, and the support portion (103) supports the support direction regulation receiving portion (124) in the support direction.

[Supplementary Note 2-8]

The connector portion according to Supplementary Note 2-6, wherein:

the elastic member (102) includes a contact direction regulation receiving portion (127) which is formed on the outer surface portion of the elastic member (102) arranged on the opposite direction side of the contact direction, and the connector portion further comprises a regulating portion (104) which supports the contact direction regulation receiving portion (127) in the contact direction.

[Supplementary Note 2-9]

The connector portion according to Supplementary Note 2-6, further comprising a wall portion arranged on the relief direction side as the opposite direction of the contact direction with respect to the elastic member (102), and wherein the elastic member (102) includes a relief portion (129) which is formed on the outer surface portion of the elastic member (102) arranged on the escape direction side and which forms the flow space (131) between itself and the wall portion.

[Supplementary Note 2-10]

The connector portion according to Supplementary Note 2-6, wherein:

the pressing force receiving portion (114) is arranged on the inner side of the device (32), the support receiving portion (116) is arranged on the outer surface portion side of the device (32), the connecting portion (58a; 58b) is electrical connecting portions (58a; 58b), the connector portion (53) includes the electrical connecting portions (58a; 58b), the elastic member (102) includes the insertion holes (117a; 117b) associated with the respective electric connecting portions (58a; 58b) and the protruding portions (121) associated with the respective insertion holes (117a; 117b), and the protruding portion (121) is formed over the entire circumference of the corresponding insertion hole (117a; 117b) as seen in the pressing direction.

[Supplementary Note 2-11]

An insertion unit of an endoscope which includes the connector portion (53) described in any one of Supplementary Notes 2-1 to 2-10, which is configured to be inserted into a body cavity, and is connected to a drive unit (32) of the endoscope (31) to receive a drive force from the drive unit (32).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electric connector portion comprising:

first and second electric contact portions;

a protective member which is movable from a protecting position where the first and second electric contact portions are protected to an opening position where the first and second electric contact portions are opened in a moving direction extending from the first electric contact portion side to the second electric contact portion side, an opening portion which is arranged with the protective member and which is configured to open the second electric contact portion when the protective member is arranged at the opening position, and a protective portion which is configured to protect the first electric contact portion when the protective member is arranged at the protecting position;

wherein the second electric contact portion is arranged on an opening direction side of the first and second electric contact portions with respect to the first electric contact portion, and the protective portion which is arranged in such a manner that it does not overlap the second electric contact portion as seen in the moving direction when the protective member is arranged at the opening position and which is formed of a sidewall portion which is substantially parallel to the moving direction and the opening direction.

2. The electrical connector portion according to claim 1, wherein:

the electric connector portion is connectable to an target electric connector portion, the moving direction substantially coincides with a connecting direction of the target electric connector portion with respect to the electric connector portion, the protective member includes a driven portion which is pressed in the connecting direction by the target electric connector portion when connecting the target electric connector portion to the electric connector portion, and the driven portion is inclined toward the opening direction of the first and second electric contact portions in the connecting direction.

3. The electric connector portion according to claim 1, further comprising:

a housing portion onto which the protective member is movably provided; and a regulation member which is provided on the housing portion, has an end portion, and is configured to revolve about the end portion between a regulating position where movement of the protective member is regulated and a releasing position where movement of the protective member is enabled, wherein the regulation member includes a slide convex portion provided at the end portion, and the housing portion includes a slide concave 10 portion which is configured to slidably support the slide convex portion to enable revolution of the regulation member about the end portion between the regulating position and the releasing position.

4. An electrical connector comprising:

the electric connector portion according to claim 1; and the target electric connector portion which is connectable to the electrical connector portion.

5. A drive unit of an endoscope which includes the electric connector portion according to claim 1 and is connected with an insertion unit of the endoscope inserted into a body cavity to give the insertion unit a drive force.

6. An endoscope comprising:

an insertion unit which includes the target electric connector portion according to claim 4 and is configured to be inserted into a body cavity; and a drive unit which includes the electric connector portion according to claim 4 and is connected with the insertion unit to give the insertion unit a drive force.

* * * * *